US008178508B2

(12) United States Patent
Schlom et al.

(10) Patent No.: US 8,178,508 B2
(45) Date of Patent: *May 15, 2012

(54) METHODS OF STIMULATING AN IMMUNE RESPONSE AGAINST PROSTATE SPECIFIC ANTIGEN

(75) Inventors: Jeffrey Schlom, Potomac, MD (US); Kwong-Yok Tsang, Bethesda, MD (US); Sam Zaremba, Rockville, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/977,660

(22) Filed: Dec. 23, 2010

(65) Prior Publication Data

US 2011/0091498 A1    Apr. 21, 2011

Related U.S. Application Data

(60) Continuation of application No. 12/479,292, filed on Jun. 5, 2009, now Pat. No. 7,871,986, which is a continuation of application No. 11/606,929, filed on Dec. 1, 2006, now Pat. No. 7,547,773, which is a division of application No. 11/114,069, filed on Apr. 26, 2005, now abandoned, which is a continuation of application No. 08/618,936, filed on Mar. 20, 1996, now Pat. No. 6,946,133.

(51) Int. Cl.
*A61K 48/00* (2006.01)
(52) U.S. Cl. .................................. 514/44 R
(58) Field of Classification Search ........................ None
See application file for complete search history.

(56) References Cited

U.S. PATENT DOCUMENTS

| 5,516,639 A | 5/1996 | Tindall et al. |
| 5,565,548 A | 10/1996 | Neurath et al. |
| 5,840,494 A | 11/1998 | Katz et al. |
| 5,925,362 A | 7/1999 | Spitler et al. |
| 6,001,349 A * | 12/1999 | Panicali et al. ............. 424/93.2 |
| 6,946,133 B1 | 9/2005 | Schlom et al. |
| 7,547,773 B2 | 6/2009 | Schlom et al. |
| 7,871,986 B2 * | 1/2011 | Schlom et al. ............. 514/44 R |

FOREIGN PATENT DOCUMENTS

| EP | 0 652 014 A1 | 10/1995 |
| WO | WO 91/02805 A2 | 3/1991 |
| WO | WO 94/03205 A1 | 2/1994 |
| WO | WO 94/20127 A1 | 9/1994 |
| WO | WO 95/04548 A1 | 2/1995 |
| WO | WO 95/28498 A1 | 10/1995 |
| WO | WO 95/28958 A1 | 11/1995 |
| WO | WO 97/03203 A2 | 1/1997 |
| ZA | 9401645 | 1/1995 |

OTHER PUBLICATIONS

Abulafia et al., *FASEB Journal*, 4(7) (Jun. 4-7, 1990) (Abstract 1896).
Akdas et al., *The Prostate*, 23: 111-113 (Mar. 1994).
Bei et al., *Journal of Clinical Laboratory Analysis*, 9: 261-268 (1995).
Bei et al., *Proceedings of the American Association for Cancer Research Annual Meeting*, 36: 664 (Mar. 1995) (Abstract 3833).
Berzofsky et al., "Immunogenicity and Antigen Structure," *Fundamental Immunology*, 2nd Ed., W.E. Paul (Editor); Raven Press Ltd., New York, 1989, pp. 169-208.
Blades et al., *Urology*, 46(5): 686-687 (Nov. 1995).
Boon, *Advances in Cancer Research*, 58: 177-210 (1992).
Bridon et al., *Urology*, 45(5): 801-806 (May 1995).
Burgess et al., *Journal of Cell Biology*, 3: 2129-2138 (Nov. 1990).
Chapdelaine et al., *International Journal of Biochemistry*, 22(1): 75-82 (1990).
Cohe et al., *Cancer Investigations*, 5: 285-291 (1987).
Correale et al., *9th International Congress of Immunology*, (Jul. 23-29, 1995) (CA Abstract 3449).
Correale et al., *Journal of Cancer Institute*, 89(4): 293-300 (Feb. 19, 1997).
Correale et al., *Proceedings of the American Association for Cancer Research*, 37: 488-499 (Mar. 21, 1996) (Abstract 3335).
Donovan et al., *Problems in Urology*, 4(3): 489-515 (Sep. 1990).
Ezzell, *Journal of NIH Research*, 7: 46-49 (1995).
Gauthier et al., *Biochimica et Biophysica Acta*, 1174: 207-210 (1993).
Hodge et al., *International Journal of Cancer*, 63: 231-237 (Oct. 9, 1995).
Karr et al., *Cancer Research*, 55(11): 2455-2462 (Jun. 1, 1995).
Karr et al., *Journal of Cellular Biochemistry Supplement*, 18D: 253 (Feb. 26-Apr. 17, 1994) (Abstract Y511).
Kurkela et al., *Biotechnology*, 13: 1230-1234 (Nov. 1995).
Lazar at al., *Molecular & Cellular Biology*, 8(3): 1247-1252 (Mar. 1988).
Lundwall et al., *FEBS Letters*, 214(2): 317-322 (Apr. 1987).
Nijman et al., *European Journal of Immunology*, 23: 1215-1219 (1993).
Ross et al., *Biotechnology Therapeutics*, 4(3&4): 187-211 (1993).
Salgaller et al., *Cancer Immunology Immunotherapy*, 39: 105-116 (1994).
Sanda et al., *Journal of the National Cancer Institute*, 87(4): 280-285 (Feb. 1995).

(Continued)

*Primary Examiner* — Albert Navarro
(74) *Attorney, Agent, or Firm* — Leydig, Voit & Mayer, Ltd.

(57) ABSTRACT

The invention provides a prostate specific antigen oligo-epitope peptide (PSA-OP) that is useful as an immunogen in the prevention or treatment of prostatic cancer and in the inhibition of prostatic cancer cells and in the establishment and characterization of PSA-specific cytotoxic T-cell lines. In particular, the invention provides methods for eliciting an immune response against PSA comprising administering (i) a priming inoculation of a first recombinant virus encoding PSA-OP and (ii) one or more boosting inoculations of a second recombinant virus encoding PSA-OP, wherein the first and second recombinant viruses are from a different genus.

18 Claims, 5 Drawing Sheets

OTHER PUBLICATIONS

Sanda et al., *The Journal of Urology*, 151: 622-628 (Mar. 1994).
Sharpe et al., *British Journal of Urology*, 74: 609-616 (Nov. 1994).
Small, *Journal of Clinical Oncology*, 22(13): 2515-2516 (2004).
Spitler, *Cancer Biotherapy*, 10: 1-3 (1995).
Vieweg et al., *Cancer Research*, 54(7): 1760-1765 (Apr. 1994).
Vieweg et al., *Cancer Research*, 55(11): 2366-2373 (Jun. 1995).
Walsh et al., *The Journal of Urology*, 151(5) (May 1994) (Abstract 106).
Wathen et al., *Journal of General Virology*, 70: 2625-2635 (1989).

\* cited by examiner

FIGURE 3

PROSTATE SPECIFIC ANTIGEN OLIGO-EPITOPE PEPTIDE

| F   | L   | T   | P   | K   | K   | L   | Q   | C   | V   |
|-----|-----|-----|-----|-----|-----|-----|-----|-----|-----|
| 141 | 142 | 143 | 144 | 145 | 146 | 147 | 148 | 149 | 150 |

| D   | L   | H   | -V  | I   | S   | N   | D   | V   | C   |
|-----|-----|-----|-----|-----|-----|-----|-----|-----|-----|
| 151 | 152 | 153 | 154 | 155 | 156 | 157 | 158 | 159 | 160 |

| A   | Q   | V   | -H  | P   | Q   | K   | V   | T   | K   |
|-----|-----|-----|-----|-----|-----|-----|-----|-----|-----|
| 161 | 162 | 163 | 164 | 165 | 166 | 167 | 168 | 169 | 170 |

(SEQ. ID NO.: 4)

FIGURE 4

| | | | | | |
|---|---|---|---|---|---|
| 5'-TTC | TTG | ACC | CCA | AAG | AAA |
| 3'-AAG | AAC | TGG | GGT | TTC | TTT |
| Phe | Leu | Thr | Pro | Lys | Lys |
| | | | | | |
| CTT | CAG | TGT | GTG | GAC | CTC |
| GAA | GTC | ACA | CAC | CTG | GAG |
| Leu | Gln | Cys | Val | Asp | Leu |
| | | | | | |
| CAT | GTT | ATT | TCC | AAT | GAC |
| GTA | CAA | TAA | AGG | TTA | CTG |
| His | Val | Ile | Ser | Asn | Asp |
| | | | | | |
| GTG | TCT | GCG | CAA | GTT | CAC |
| CAC | ACA | CGC | GTT | CAA | GTG |
| Val | Cys | Ala | Gln | Val | His |
| | | | | | |
| CCT | CAG | AAG | GTG | ACC | AAG-3' (SEQ. ID NO.: 5) |
| GGA | GTC | TTC | CAC | TGG | TTC-5' (SEQ. ID NO.: 6) |
| Pro | Gln | Lys | Val | Thr | Lys (SEQ. ID NO.: 4) |

FIGURE 5

```
>kpn-1_site
         10         20         30         40         50         60         70         80         90
    *         *         *         *         *         *         *         *         *
GACTCAGGTA CCACCATGAG GTACATGATT TTAGGCTTGC TCGCCCTTGC GGCAGTCTGC AGCGCTGATA TGTTTAATAA TTTTACCGTT
CTGAGTCCAT GGTGGTACTC CATGTACTAA AATCCGAACG AGCGGGAACG CCGTCAGACG TCGCGACTAT ACAAATTATT AAAATGGCAA
                     >
         d    10    d         E3/19K SIGNAL      d    40    d    50    >
                                                                                1 TO 72 OF TT-CD4
                                                                             f    >
                                                                                     TT CD2 EPITO
         c          FULL CODING REGION [SPLIT]                 c         >

100        110        120        130        140        150        160        170        180
    *         *         *         *         *         *         *         *         *
AGCTTTTGGT TGAGGGTTCC TAAAGTATCT GCTAGTCATT TAGAACAAGA GTTCTTGACC CCAAAGAAAC TTCAGTGTGT GGACCTCCAT
TCGAAAACCA ACTCCCAAGG ATTTCATAGA CGATCAGTAA ATCTTGTTCT CAAGAACTGG GGTTTCTTTG AAGTCACACA CCTGGAGTTA
                                              b    10    b   PSA AA490-594   30   b         40   >
    30    e    4_1 TO 72 OF TT-CD4    60    e    70   >
    20    g30       TT CD4 EPITOPE_g50    g60         >
           F   L   T   P   K   K   L   Q   C   V   D   L   H 190        200        210        220        230        240        250        260
    *         *         *         *         *         *         *         *
GTTATTCCA ATGACGTGTG TGCCCAAGTT CACCCTCAGA AGGTGACCAA GTTCATGCTG TGTTAGTTTT TGTCTCGAGC TGCAG
CAATAAGGT TACTGCACAC ACGGGTTCAA GTGGGAGTCT TCCACTGGTT CAAGTACGAC ACAATCAAAA ACAGACTCG ACGTC\
         b   60   b         PSA AA490-594   b   90   b         100   b             >
    50   b
   V   I   S   N   D   V   C   A   Q   V   H   P   Q   K   V   T   K    *
                                                        >xho-1_site
                                                                                        h    >
```

METHODS OF STIMULATING AN IMMUNE RESPONSE AGAINST PROSTATE SPECIFIC ANTIGEN

This patent application is a continuation of U.S. patent application Ser. No. 12/479,292, filed on Jun. 5, 2009, now U.S. Pat. No. 7,871,986, which is a continuation of U.S. patent application Ser. No. 11/606,929, filed Dec. 1, 2006, now U.S. Pat. No. 7,547,773, which is a divisional of U.S. patent application Ser. No. 11/114,069, filed Apr. 26, 2005, now abandoned, which is a continuation of U.S. patent application Ser. No. 08/618,936, filed Mar. 20, 1996, now U.S. Pat. No. 6,946,133, which applications are all incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 5,117 Byte ASCII (Text) file named "707323_ST25.txt," created on Dec. 22, 2010.

FIELD OF THE INVENTION

The present invention relates generally to generation of cellular and humoral immune responses to a mammalian prostate-specific antigen (PSA). More specifically, the present invention relates to a prostate specific antigen (PSA) oligo-epitope peptide useful in generating PSA specific T lymphocytes for prevention or treatment of prostate cancer.

BACKGROUND OF THE INVENTION

Cancer of the prostate is the most commonly diagnosed cancer in men and is the second most common cause of cancer death (Carter et al, 1990; Armbruster et al, 1993). If detected at an early stage, prostate cancer is potentially curable. However, a majority of cases are diagnosed at later stages when metastasis of the primary tumor has already occurred (Wang et al, 1982). Even early diagnosis is problematic because not all individuals who test positive in these screens develop cancer. Present treatment for prostate cancer includes radical prostatectomy, radiation therapy, or hormonal therapy. No systemic therapy has clearly improved survival in cases of hormone refractory disease. With surgical intervention, complete eradication of the tumor is not always achieved and the observed re-occurrence of the cancer (12-68%) is dependent upon the initial clinical tumor stage (Zietman et al, 1993). Thus, alternative methods of treatment including prophylaxis or prevention are desirable.

Prostate specific antigen (PSA) is a 240 amino acid member of the glandular kallikrein gene family. (Wang et al, 1982; Wang et al, 1979; Bilhartz et al, 1991). PSA is a serine protease, produced by normal prostatic tissue, and secreted exclusively by the epithelial cells lining prostatic acini and ducts (Wang et al, 1982; Wang et al, 1979; Lilja et al, 1993). Prostatic specific antigen can be detected at low levels in the sera of healthy males without clinical evidence of prostate cancer. However, during neoplastic states, circulating levels of this antigen increase dramatically, correlating with the clinical stage of the disease (Schellhammer et al, 1993; Huang et al, 1993; Kleer et al, 1993; Oesterling et al, 1991). Prostatic specific antigen is now the most widely used marker for prostate cancer. The tissue specificity of this antigen makes PSA a potential target antigen for active specific immunotherapy (Armbruster et al, 1993; Brawer et al, 1989), especially in patients who have undergone a radical prostatectomy in which the only PSA expressing tissue in the body should be in metastatic deposits. Recent studies using in-vitro immunization have shown the generation of CD4 and CD8 cells specific for PSA (Peace et al, 1994; Correale et al, 1995). However, although weak natural killer cell responses have been occasionally documented in prostate cancer patients (Choe et al, 1987), attempts to generate an in vivo immune response have met with limited success. For example, several attempts to actively immunize patients with prostate adenocarcinoma cells admixed with Bacillus Calmette-Gurein (BCG) have shown little or no therapeutic benefit (Donovan et al, 1990). The ability to elicit an immune response as a result of exposure to PSA in vivo would be extremely useful.

Vaccinia virus has been used in the world-wide eradication of smallpox. This virus has been shown to express a wide range of inserted genes, including several tumor associated genes such as p97, HER2/neu, p53 and ETA (Paoletti et al, 1993). Other pox viruses that have been suggested as useful for expression of multiple genes include avipox such as fowl pox. Cytokines expressed by recombinant vaccinia virus include IL-1, IL-2, IL-5, IL-6, TNF-α and IFN-γ (Paoletti et al, 1993). Recombinant pox viruses, for example vaccinia viruses, are being considered for use in therapy of cancer because it has been shown in animal models that the co-presentation of a weak immunogen with the highly immunogenic poxvirus proteins can elicit a strong immune response against the inserted gene product (Kaufman et al, 1991, Paoletti et al, 1993; Kantor et al, 1992a; Kantor et al, 1992b; Irvine et al, 1993; Moss et al, 1993). A recombinant vaccinia virus containing the human carcinoembryonic antigen gene has just completed phase 1 clinical trials in carcinoma patients with no evidence of toxicity other than that observed with the wild type smallpox vaccine (Kantor et al, 1992b).

Currently, models for the evaluation of prostate therapeutics include the canine (McEntee et al, 1987) and the Dunning rat (Isaacs et al, 1986); neither of these models, however, are practical for the study of PSA-recombinant vaccines due to the very low homology of rat and canine PSA to human PSA (Karr et al, 1995; Schroder et al, 1982). In contrast, the prostate gland of the rhesus monkey is structurally and functionally similar to the human prostate (Wakui et al, 1992). At the molecular level there is 94% homology between either the amino acid or nucleic acid sequences of rhesus PSA (Gauther et al, 1993) and those sequences of human prostate specific antigen (Karr et al, 1995; Lundwall et al, 1987). Thus, human PSA is essentially an autoantigen in the rhesus monkey. Accordingly, the rhesus monkey can serve as a model for autologous anti-PSA immune reactions.

Since PSA shares extensive homology with members of the kallikrein gene family which are expressed in normal tissue, it is important to use minimal epitope peptides to avoid unwarranted cross reactivity. These epitopes have been selected for their divergence with members of the kallikrein gene family.

Studies disclosed in U.S. Ser. No. 08/500,306 have shown that two PSA epitope peptides (PSA-1 and PSA-3), 10-mers selected to conform to human HLA class 1-A2 motifs, can elicit CTL responses in both normal donors and patients with prostate cancer. (Correale et al, 1995) The present invention discloses the advantage of PSA-oligo-epitope peptides comprising more than one PSA epitope peptide in generating PSA specific cellular immune responses.

SUMMARY OF THE INVENTION

The invention is a prostate specific antigen oligo-epitope peptide and analogs thereof which are immunogenic amongst individuals with at least one HLA-class I allele, preferably more than one HLA-class I allele. The prostate specific antigen oligo-epitope peptide comprises more than one 8 to 12 mer PSA epitope peptide adjoined together, each 8 to 12 mer PSA epitope peptide binds to a human HLA class I molecule type. The 8 to 12 mer PSA epitope peptides may be adjoined via a short amino acid sequence.

The prostate specific antigen oligo-epitope peptide and analogs thereof elicit PSA specific cytotoxic T lymphocytes which lyse cells having bound thereto PSA, fragments of PSA, or one or more PSA epitope peptides thereof.

Another object of the invention is a pharmaceutical composition comprising a prostate specific antigen oligo-epitope peptide or analogs thereof and a pharmaceutically acceptable carrier. The pharmaceutical composition is useful as an immunogen and as a therapeutic in the prevention or treatment of prostate cancer and in inhibiting growth of PSA$^+$ cancer cells.

Another aspect of the invention is a method of generating PSA specific cytotoxic T lymphocytes by in vivo administration of an effective amount of a prostate specific antigen oligo-epitope peptide or analogs thereof, alone or in combination with an adjuvant or liposomes. The PSA specific cytotoxic T lymphocytes which arise from immunization are useful in methods of inhibiting or killing PSA positive tumor cells in a mammal.

Yet another aspect of the invention is a method of generating PSA specific cytotoxic T lymphocytes in vitro by stimulation of lymphocytes from a source with an effective amount of a prostate specific antigen oligo-epitope peptide or analogs thereof, alone or in combination with one or more cytokines to generate PSA specific cytotoxic T lymphocytes. Such PSA specific cytotoxic T lymphocytes may be adoptively transferred into a mammal for the prevention or treatment of prostate cancer and for inhibiting or killing PSA positive tumor cells.

A further object of the invention is a DNA sequence encoding a prostate specific antigen oligo-epitope peptide comprising more than one 8 to 12 mer PSA epitope peptide or analogs thereof, each 8 to 12 mer PSA epitope peptide binds to a human HLA class I molecule type.

An object of the invention is a vector comprising at least one insertion site containing a DNA sequence encoding a prostate specific antigen oligo-epitope peptide or analogs thereof, operably linked to a promoter capable of expression in a host cell.

Another aspect of the invention is a method of generating PSA specific cytotoxic T lymphocytes by administration into a mammalian host an effective amount of a recombinant virus vector comprising at least one insertion site containing a DNA sequence encoding a prostate specific antigen oligo-epitope peptide or analogs thereof.

We have discovered that by using a recombinant viral vector, preferably a pox virus vector having at least one insertion site containing a DNA segment encoding prostate-specific antigen (PSA), or a cytotoxic T-cell eliciting epitope thereof, operably linked to a promoter capable of expression in the host, a specific humor and cellular immune response to PSA can be generated. The method preferably comprises introducing a sufficient amount of the recombinant pox virus vector into a host to stimulate the immune response, and contacting the host with additional PSA at periodic intervals thereafter. The additional PSA, or a cytotoxic T-cell eliciting epitope thereof, may be added by using a second pox virus vector from a different pox genus. In another embodiment, additional PSA can be added by contacting the host with PSA by a variety of other methods, including in one preferred embodiment adding PSA. The PSA may be formulated with an adjuvant or in a liposomal formulation.

In a further embodiment, an immune response to PSA can be generated by contacting the host initially with a sufficient amount of PSA, or a cytotoxic T-cell eliciting epitope thereof, to stimulate an immune response and at periodic intervals thereafter contacting the host with additional PSA. The additional PSA, or a cytotoxic T-cell generating fragment thereof, may be added using a pox virus vector as discussed above.

We have also discovered that human cytotoxic T-cells specific for PSA can be produced using a cytotoxic T-cell eliciting epitope of the PSA and that these cells have the ability to lyse PSA-expressing human prostate carcinoma cells.

As used herein the term "prostate specific antigen" includes the native protein whether purified from a native source or made by recombinant technology, as well as any polypeptide, mutein, or portion derived therefrom that is capable of generating an immune response to a native conformationally correct PSA. For example, one can make conservative amino acid substitutions in the molecule without adversely affecting the ability to use the recombinant to generate an antibody that will also recognize native PSA.

The pox virus is preferably selected from the group of pox viruses consisting of suipox, avipox, capripox and orthopox virus. Preferred orthopox include vaccinia, rabbit pox and raccoon pox. Preferred avipox includes fowlpox, canary pox and pigeon pox. A more preferred avipox is fowlpox. The preferred suipox is swinepox.

Vaccinia viral vectors may elicit a strong antibody response. Thus, while numerous boosts with vaccinia vectors are possible, its repeated use may not be preferred in certain instances. We have discovered that by using pox from different genera to boost, this sensitivity problem can be minimized. In accordance with the present invention, in order to avoid such problems, preferably, when the first or initial pox virus vector is vaccinia, the second and subsequent pox virus vectors are selected from the pox viruses from a different genus such as suipox, avipox, capripox or an orthopox immunogenically distinct from vaccinia.

Adjuvants include, for example, RIBI Detox, QS21, alum and incomplete Freund's adjuvant. Liposomal formulations can also be used.

Human cytotoxic T-cells specific for PSA produced in accordance with the present invention can be isolated from a human host. These cells can be used in drug assays, used to map cytotoxic T-cells eliciting antigen epitopes or in adoptive cell therapy.

BRIEF DESCRIPTION OF THE DRAWINGS

In FIG. 2A, the area of lesions was measured 7 days following each inoculation of rhesus monkeys with either V-Wyeth (open circles) or rV-PSA (closed circles). In FIG. 2B, the duration of the lesion was monitored as time of scab disappearance. In FIG. 2C, the extent of lymph node swelling was recorded and characterized as very swollen (3+), i.e. more than two axillary nodes swollen; swollen (2+), i.e. one or two nodes easily palpable; marginally swollen (1+), i.e. one node was barely palpable or not swollen (0), 7 days following inoculation with vaccinia virus. Each symbol represents one monkey.

FIG. 3 shows the amino acid sequence of a prostate specific antigen oligo-epitope peptide.

FIG. 4 shows the nucleic acid sequence encoding a prostate specific antigen oligo-epitope peptide.

FIG. 5 shows the nucleic acid sequence of an insert (within the Kpn-1 site and the Xho-1 site) cloned into recombinant vaccinia comprising the nucleic acid sequence encoding a prostate specific antigen oligo-epitope peptide (PSA AA490-594), an endoplasmic reticulum trafficking signal (E3/19K signal), and a universal T helper epitope peptide, tetanus toxoid CD4 epitope (TT CD4 epitope). The 5'→3' insert has SEQ. ID NO.: 14. The complementary 3'→5' insert has SEQ. ID NO.: 15.

DETAILED DESCRIPTION OF THE INVENTION

Figure 1:
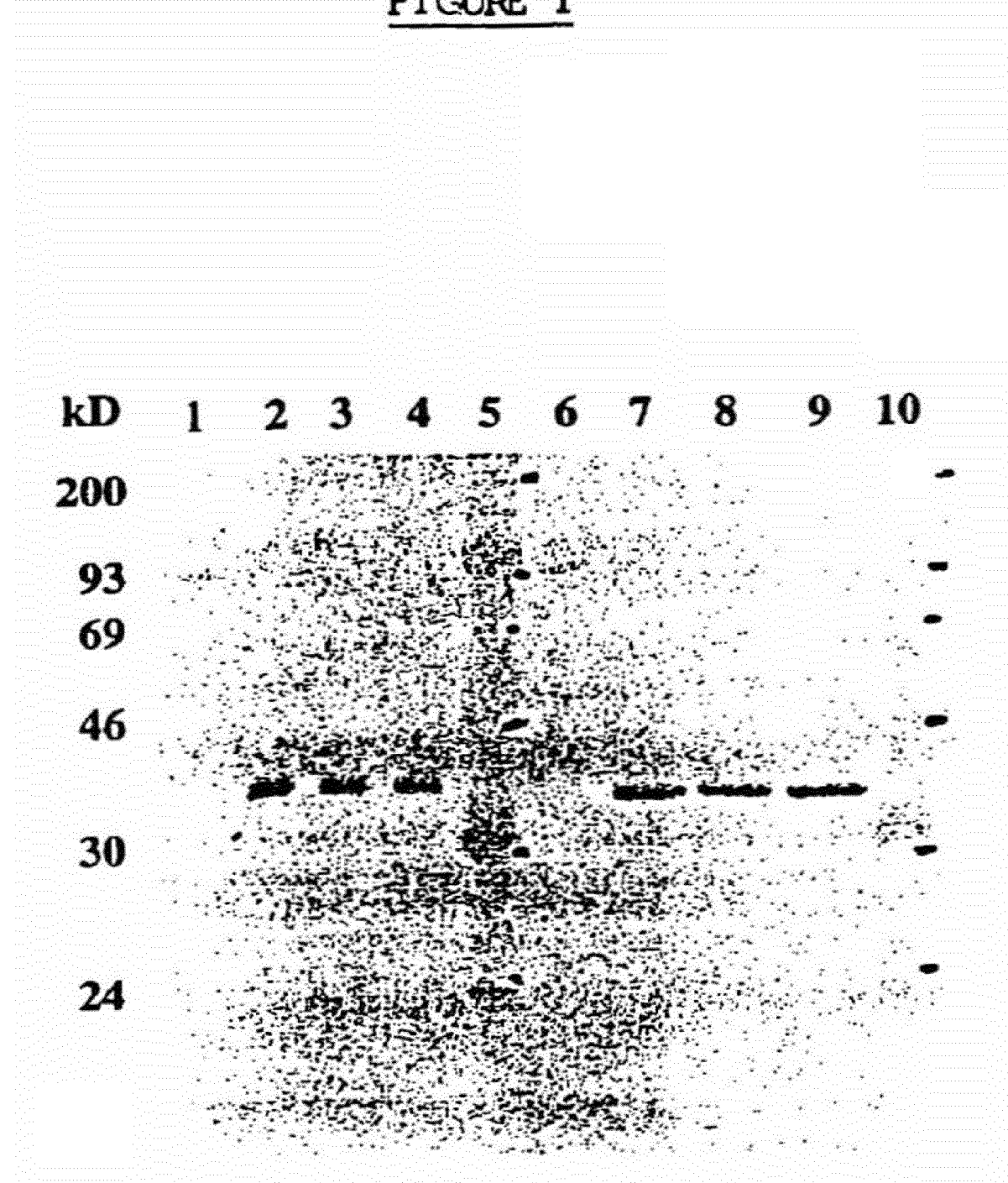
FIG. 1 shows a Western blot of PSA from rV-PSA infected BSC-40 cells. Lanes 2-4 are extracts from supernatant fluid from cells infected overnight with rV-PSA at an MOI of 1, while Lanes 7-9 are extracts from the corresponding infected cells. Lanes 1 and 6 are supernatant extracts and cell extracts from V-Wyeth infected cells. Blot was developed using a specific MAb for human PSA. This blot illustrates that cells infected with rV-PSA authentically express and secrete the 33 kD PSA protein.

The invention is a prostate specific antigen (PSA) oligo-epitope peptide. The prostate specific antigen oligo-epitope peptide is characterized by its ability to elicit a cellular immune response specific against PSA or portion thereof and against cells expressing or binding PSA or portion thereof in a mammalian host.

In general, tumor associated antigen proteins, such as PSA protein, are processed by intracellular proteases into small epitope peptides which are then transported to the cell surface bound tightly in a cleft on the HLA class I molecule. T cells recognize these small epitope peptides only when they are bound within this cleft on the target cell. The class I molecules of the major histocompatibility complex (MHC) are found on the surfaces of cells including tumor cells and are the self molecules recognized in conjunction with antigen by cytotoxic T cells.

As disclosed herein, short PSA epitope peptides composed of an amino acid sequence of about 9 to 10 amino acids bind directly within the cleft of an HLA class I molecule without intracellular processing. Two such PSA epitope peptides, PSA-1 and PSA-3 are bound by one specific HLA class I molecule type, i.e. HLA-class I-A2. Each of these individual PSA epitope peptides elicits PSA specific cytotoxic T cells which lyse PSA$^+$ HLA-class I-A2 target cells.

However, due to polymorphisms within the peptide binding cleft of class I molecules there are variations among individuals in the ability of their class I molecule types to bind antigens. Thus, while 9 mer and 10 mer PSA epitope peptides are effective in generating cytotoxic T lymphocytes in individuals having a HLA-class I A2 type, the same 9 mer and 10 mer PSA epitope peptides may not be effective or may be less effective in generating cytotoxic T lymphocytes in individuals having different interactions of HLA-peptide complexes with different T-cell receptor molecules, which can differ amongst individuals.

The prostate specific antigen oligo-epitope peptide and analogs thereof of the present invention which comprises more than one 8 to 12 mer PSA epitope peptides linked together has the advantage of eliciting cellular immune responses in individuals having diverse HLA class I molecule types or alleles. The prostate specific antigen oligo-epitope peptide is processed by extracellular proteases or other mechanisms allowing the resulting PSA epitope peptide cleavage fragments to bind to the cleft of the same or several different HLA class I molecule types.

Thus, the prostate specific antigen oligo-epitope peptide, in contrast to shorter individual PSA epitope peptides of about 8 to 12 mer, is immunogenic for a broad segment of the human population with differing HLA class I molecule types and differing T-cell receptor interactions with HLA class-I peptide complexes.

The prostate specific antigen oligo-epitope peptide comprises peptide sequences which fit the consensus motif for at least one HLA class I molecule type, and preferably contains peptide sequences that fit the consensus motif of more than one HLA class I molecule type.

In one embodiment, the prostate specific antigen oligo-epitope peptide comprises more than one 8 to 12 mer PSA epitope peptide sequence which fits the consensus motif for one or more of the HLA class I molecule types, which include but are not limited to HLA-A1, HLA-A2, A3, A11, HLA-A24, HLA-A26, HLA-A28, HLA-A32, HLA-B7, HLA-B44, HLA-Cw3, HLA-Cw4, HLA-Cw5, Aw68 and B53.

In another embodiment, the prostate specific antigen oligo-epitope peptide comprises PSA peptide sequences which fit the consensus motif for HLA-A2, A.3, A11 and B53. HLA class I molecule type, HLA-A3 is present in 26 and 17% of North American caucasians and blacks respectively. HLA class I molecule type, HLA-A11 is present in 40% of the Asian population, and HLA-53 is present in 22% of blacks. Thus, the prostate specific antigen oligo-epitope peptide is useful in generating a cellular immune response against PSA in a broad segment of the human population with differing HLA class I molecule types.

Individual 9 mer and 10 mer amino acid PSA epitope peptides are capable of generating cytotoxic T lymphocytes (CTLs) in vitro and capable of pulsing target cells for lysis by PSA-specific CTLs. Modeling studies have shown that the individual 9 mer or 10 mer PSA epitope peptides fits into the groove of a unique class I HLA molecule, A2. The present invention of linking various combinations of 8 to 12 mer PSA epitope peptides allows for one immunogen instead of two or more separate immunogens, as the oligo-epitope peptide is efficiently processed by proteases at the antigen presenting cell surface or target cell surface, or processed by other mechanisms to form appropriate smaller PSA epitope peptide cleavage fragments that interact or bind with the same class I molecule type or with a variety of class I molecule types resulting in the generation of a PSA specific cellular response in the majority of the human population.

The PSA oligo-epitope peptide or analogs thereof generate cytotoxic T lymphocytes which inhibit or lyse target cells which express or have bound thereto PSA and target cells which express or have bound thereto one, preferably more than one 8 to 12 mer PSA epitope peptides. Additionally, target cells inhibited or lysed by the cytotoxic T lymphocytes may have one HLA class I molecule type or a plurality HLA class I molecule types.

The prostate specific antigen oligo-epitope peptide, analog or functional equivalent thereof comprise more than one 8 to 12 mer PSA epitope peptide which conforms to at least one human HLA class I molecule type, preferably more than one human HLA class I molecule types. A first PSA epitope peptide that conforms to a human HLA class I molecule type is adjoined to a second PSA epitope peptide that conforms to a human HLA class I molecule type. The first and second epitope peptides may be joined together directly or optionally joined together via a short amino acid linker sequence. The peptides are joined together by peptide bonds.

The individual PSA epitope peptides which comprise the prostate specific antigen oligo-epitope peptide may each vary in the number of amino acids but typically comprise about 8 to about 12 amino acids, preferably about 9 to about 10 amino acids. In one embodiment, the first and second PSA epitope peptide each comprise about 10 amino acids.

The prostate specific antigen oligo-epitope peptide may comprise repeating units of the individual PSA epitope peptide, or combinations of repeating units. The total number of repeating units in the prostate specific antigen oligo-epitope peptide of individual PSA epitope peptides or combinations of PSA epitope peptides may be about 6 to about 8.

When utilized, the amino acid linker sequence for joining the 8 to 12 mer PSA epitope peptides comprises about 1 to about 10 amino acids, preferably about 1 to about 5 amino acids. In one embodiment, the linker comprises about three amino acids. In a particular embodiment, the linker sequence comprises Asp-His-Leu. The amino acid linker sequence is cleavable by proteolytic activity.

In one embodiment, the prostate specific antigen oligo-epitope peptide comprises one or more PSA1 peptides having SEQ. ID No.: 1 or analogs thereof and one or more PSA2 peptides having SEQ. ID No.: 2 or analogs thereof. In a preferred embodiment, the prostate specific antigen oligo-epitope peptide comprises one PSA1 peptide and one PSA2 peptide linked together.

Additionally, the prostate specific antigen oligo-epitope peptide comprises one or more additional PSA epitope peptides adjoined to the second PSA epitope peptide. In one embodiment, a third PSA peptide comprises an amino acid sequence which overlaps the sequence at the carboxyl terminus of the second PSA epitope peptide. The overlap in sequence may be by one to three amino acids. In one embodiment, the overlap is by two amino acids. In a particular embodiment, a third PSA epitope peptide comprises QVH-PQKVTK (SEQ. ID NO.: 3) in which the overlapping sequence is QV.

In a preferred embodiment, the oligo-epitope peptide comprises the amino acid sequence:

```
FLTPKKLQCVDLHVISNDVCAQVHPQKVTK    (Seq. ID No.: 4)
``` and analogs and variants thereof. In one embodiment, the prostate specific antigen oligo-epitope peptide comprises analogs with substitutions that include but are not limited to valine at one or more positions at amino acid residue positions 148, 149, 160 and/or 161. In yet another embodiment, the prostate specific antigen comprises analogs with deletions that include but are not limited to deletion of one or more amino acids at positions 151, 152 and 153.

The prostate specific antigen oligo-epitope peptide may be obtained by recombinant DNA technology, by chemical peptide synthesis or by appropriate protease cleavage of the isolated, natural PSA.

The prostate specific antigen oligo-epitope peptide or analogs thereof of the present invention may be formulated into a pharmaceutical composition in combination with a pharmaceutically acceptable carrier for use as an immunogen in a mammal, preferably a human or primate. The composition may further comprise one or more other constituents to enhance the immune response which include but are not limited to biological response modifiers such as interleukin 2, interleukin 6, interleukin 12, interferon, tumor necrosis factor, GM-CSF and cyclophosphamide.

The prostate specific antigen oligo-epitope peptide is administered to a mammal in an amount effective in generating a PSA specific cellular immune response. The efficacy of the prostate specific antigen oligo-epitope peptide as an immunogen may be determined by in vivo or in vitro parameters as are known in the art. These parameters include but are not limited to antigen specific cytotoxicity assays, regression of PSA⁺ tumors, inhibition of PSA⁺ cancer cells, production of cytokines and the like.

The prostate specific antigen oligo-epitope peptide may be administered in a dose of about 0.5 mg to about 100 mg per kilogram body weight of the mammal. Several doses may be provided over a period of weeks as indicated. The PSA-OP or analogs thereof may be administered alone or in combination with adjuvants, liposomes, cytokines, biological response modifiers, or other reagents in the art that are known to enhance immune responses.

The PSA-OP may also be conjugated to other helper peptides or to larger carrier molecules to enhance the immunogenicity of the peptide. These molecules include but are not limited to influenza peptide, tetanus toxoid, tetanus toxoid CD4 epitope, *Pseudomonas* exotoxin A, poly-L-lysine, and the like.

The invention also provides a method of generating PSA specific cytotoxic T lymphocytes in vivo or in vitro by stimulation of lymphocytes from a source with an effective amount of a prostate specific antigen oligo-epitope peptide alone or in combination with one or more cytokines in context of an HLA class I molecule to generate PSA specific cytotoxic T lymphocytes. The sources of lymphocytes include but are not limited to peripheral blood lymphocytes, tumor infiltrating lymphocytes, lymph nodes and the like.

The invention encompasses a DNA sequence and analog and variant thereof which encodes a prostate specific antigen oligo-epitope peptide or analog thereof. In one embodiment the DNA sequence comprises:

```
5'-TTC TTG ACC CCA AAG AAA        (SEQ.ID NO.: 5)
3'-AAG AAC TGG GGT TTC TTT        (SEQ.ID NO.: 6)
   Phe Leu Thr Pro Lys Lys        (SEQ.ID NO.: 4)

CTT CAG TGT GTG GAC CTC
   GAA GTC ACA CAC CTG GAG
   Leu Gln Cys Val Asp Leu

CAT GTT ATT TCC AAT GAC
   GTA CAA TAA AGG TTA CTG
   His Val Ile Ser Asn Asp

GTG TCT GCG CAA GTT CAC
   CAC ACA CGC GTT CAA GTG
   Val Cys Ala Gln Val His

CCT CAG AAG GTG ACC AAG-3'
   GGA GTC TTC CAC TGG TTC-5'
   Pro Gln Lys Val Thr Lys
``` and analogs and variants thereof.

Included in the ambit of the invention are substitutions and deletions within the DNA sequence provided that the modifications result in a functionally equivalent PSA-OP peptide or a peptide with enhanced immunogenicity. In one embodiment a DNA sequence is substituted with the appropriate nucleic acids that encode analogs of the prostate specific antigen oligo-epitope peptide based on codon degeneracy as are known in the art. Other substitutions in the DNA sequence include but are not limited to valine at one or more positions at amino acid residue position 148, 149, 160 and/or 161.

The invention further encompasses vectors and plasmids comprising a DNA sequence, analog or variant thereof which encodes a prostate specific antigen oligo-epitope peptide. The vectors may further comprise one or more DNA sequences encoding helper peptides or large carrier molecule(s) to enhance the immunogenicity of the PSA-OP. These additional DNA sequences encode molecules that include but are not limited to influenza peptide, tetanus toxoid, tetanus toxoid CD4 epitope, *Pseudomonas* exotoxin A, poly-L-lysine, and the like. In one embodiment, the vector further comprises a tetanus toxoid CD4 epitope.

Of particular interest are recombinant viral vectors comprising a DNA sequence, analog or variant thereof which encodes a prostate specific antigen oligo-epitope peptide or analogs thereof. In one embodiment, the recombinant viral vector further comprises a tetanus toxoid CD4 epitope. In a particular embodiment, the recombinant viral vector is recombinant vaccinia comprising a DNA sequence encoding a prostate specific antigen oligo-epitope peptide, a DNA sequence encoding endoplasmic reticulum trafficking signal, and a DNA sequence encoding tetanus toxoid CD4 epitope as depicted in FIG. 5.

Host cells which may express the DNA encoding the prostate specific antigen oligo-epitope peptide or analogs thereof carried by vectors or plasmids are prokaryotic and eukaryotic host cells and include but are not limited to *E. coli, Listeria, Bacillus* species, COS cells, CV-1, Vero cells, BSC-40 cells, HuTk143 cells, chick embryo fibroblasts, prostatic cells, tumor cells, antigen presenting cells and the like. When the host cells is an antigen presenting cell or a target cell, the host cell should additionally express a MHC class I molecule.

We have induced an immune response specific to PSA in the rhesus monkey model by placing the PSA gene into a recombinant viral vector, i.e. a pox vector such as vaccinia virus.

Additionally, an immune response to PSA can be generated by contacting the host initially with a sufficient amount of PSA, or a cytotoxic T-cell eliciting epitope thereof, to stimulate an immune response and at periodic intervals thereafter contacting the host with additional PSA. The additional PSA, or a cytotoxic T-cell generating fragment thereof, may be added using a pox virus vector.

A DNA fragment encoding the open reading frame of human PSA can be obtained, for example, from total RNA extracted from the human metastatic prostate adenocarcinoma cell line, LNCaP.FGC (CRL 1740, American Type Cell Culture (ATCC), Rockville, Md.) by reverse transcriptase PCR using PSA specific oligonucleotide primers 5' TCTAGAAGCCCCAAGCTTACCACCTGCA 3' (SEQ. ID. NO.: 16), 5' TCTAGATCAGGGGTTGGCCACGATGGT-GTCCTTGATCCACT 3' (SEQ. ID. NO.: 17). The nucleotide sequence of the PSA cDNA has been published (Lundwall et al, 1987).

Recombinant human PSA can be obtained using a baculovirus expression system in accordance with the method of Bei et al, *J. Clin. Lab. Anal.*, 9:261-268 (1995), the disclosure of which is herein incorporated by reference.

Viral Vector

Basic techniques for preparing recombinant DNA viruses containing a heterologous DNA sequence encoding the carcinoma self-associated antigen or cytotoxic T-cell eliciting epitope are known to the skilled artisan and involve, for example, homologous recombination between the viral DNA sequences flanking the DNA sequence in a donor plasmid and homologous sequences present in the parental virus (Mackett et al, *Proc. Natl. Acad. Sci.* USA 79:7415-7419 (1982)). For example, recombinant viral vectors such as a pox viral vector can be used in delivering the gene. The vector can be constructed for example by steps known in the art, e.g. analogous to the methods for creating synthetic recombinants of the fowlpox virus described in U.S. Pat. No. 5,093,258, the disclosure of which is incorporated herein by reference. Other techniques include using a unique restriction endonuclease site that is naturally present or artificially inserted in the parental viral vector to insert the heterologous DNA.

Pox viruses useful in practicing the present invention include orthopox, suipox, avipox and capripox virus. Orthopox include vaccinia, ectromelia and raccoon pox. The preferred orthopox is vaccinia.

Avipox includes fowlpox, canary pox and pigeon pox. The preferred avipox is fowlpox.

Capripox include goatpox and sheeppox.

A preferred suipox is swinepox.

Other viral vectors that can be used include other DNA viruses such as herpes virus and adenoviruses, and RNA viruses such as retroviruses and polio.

For example, the DNA gene sequence to be inserted into the virus can be placed into a donor plasmid, e.g. an *E. coli* plasmid construct, into which DNA homologous to a section of DNA such as that of the insertion site of the poxvirus where the DNA is to be inserted has been inserted. Separately the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA which is the desired insertion region. With a parental pox viral vector, a pox promoter is used. The resulting plasmid construct is then amplified by growth within *E. coli* bacteria and isolated. Preferably, the plasmid also contains an origin of replication such as the *E. coli* origin of replication, and a marker such as an antibiotic resistance gene for selection and propagation in *E. coli*.

Second, the isolated plasmid containing the DNA gene sequence to be inserted is transfected into a cell culture, e.g. chick embryo fibroblasts, along with the parental virus, e.g. poxvirus. Recombination between homologous pox DNA in the plasmid and the viral genome respectively results in a recombinant poxvirus modified by the presence of the promoter-gene construct in its genome, at a site which does not affect virus viability.

As noted above, the gene is inserted into a region (insertion region), in the virus which does not affect virus viability of the resultant recombinant virus. The skilled artisan can readily identify such regions in a virus by, for example, randomly testing segments of virus DNA for regions that allow recombinant formation without seriously affecting virus viability of the recombinant. One region that can readily be used and is present in many viruses is the thymidine kinase (TK) gene. For example, the TK gene has been found in all pox virus genomes examined [leporipoxvirus: Upton et al, *J. Virology*, 60:920 (1986) (shope fibroma virus); capripoxvirus: Gershon et al, *J. Gen. Virol.*, 70:525 (1989) (Kenya sheep-1); orthopoxvirus: Weir et al, *J. Virol.*, 46:530 (1983) (vaccinia); Esposito et al, *Virology*, 135:561 (1984) (monkeypox and variola virus); Hruby et al, *PNAS*, 80:3411 (1983) (vaccinia); Kilpatrick et al, *Virology*, 143:399 (1985) (Yaba monkey tumor virus); avipoxvirus: Binns et al, *J. Gen. Virol.* 69:1275 (1988) (fowlpox); Boyle et al, *Virology*, 156:355 (1987) (fowlpox); Schnitzlein et al, *J. Virological Methods*, 20:341 (1988) (fowlpox, quailpox); entomopox (Lytvyn et al, *J. Gen. Virol.*, 73:3235-3240 (1992)].

In vaccinia, in addition to the TK region, other insertion regions include, for example, the Hind III M fragment.

In fowlpox, in addition to the TK region, other insertion regions include, for example, the BamHI J fragment [Jenkins et al, *AIDS Research and Human Retroviruses* 7:991-998 (1991)] the EcoRI-HindIII fragment, EcoRV-HindIII fragment, BamHI fragment and the HindIII fragment set forth in EPO Application No. 0 308 220 A1. [Calvert et al, *J. of Virol.* 67:3069-3076 (1993); Taylor et al, *Vaccine* 6:497-503 (1988); Spehner et al (1990) and Boursnell et al, *J. of Gen. Virol.* 71:621-628 (1990)].

In swinepox preferred insertion sites include the thymidine kinase gene region.

In addition to the requirement that the gene be inserted into an insertion region, successful expression of the inserted gene by the modified poxvirus requires the presence of a promoter operably linked to the desired gene, i.e. in the proper relationship to the inserted gene. The promoter must be placed so that it is located upstream from the gene to be expressed. Promoters are well known in the art and can readily be selected depending on the host and the cell type you wish to target. For example in poxviruses, pox viral promoters should be used, such as the vaccinia 7.5 k, 40K or fowlpox promoters such as FPV C1A. Enhancer elements can also be used in combination to increase the level of expression. Furthermore, the use of inducible promoters, which are also well known in the art, in some embodiments are preferred.

A specific immune response for PSA can be generated by administering between about $10^5$-$10^9$ pfu of the recombinant pox virus, constructed as discussed above to a host, more preferably one uses $10^7$ pfu. The preferred host is a human. At least one interval thereafter, which is preferably one to three months later, the immune response is boosted by administering additional antigen to the host. More preferably there is at least a second "boost" preferably one to three months after the first boost. The antigen may be administered using the same pox virus vector. The antigen may preferably be administered using a second pox virus vector from a different pox genera, or may be administered directly using, for example, an adjuvant or liposome. Cytokines, e.g. IL-2, IL-6, IL-12 or co-stimulatory molecules, e.g. B7.1, B7.2 may be used as biologic adjuvants and can be administered systemically to the host or co-administered via insertion of the genes encoding the molecules into the recombinant pox vector.

Adjuvants include, for example, RIBI Detox (Ribi Immunochemical), QS21 and incomplete Freund's adjuvant.

Generation of Cytotoxic T-Cells

Cytotoxic T-cells specific for PSA can be established from peripheral blood mononuclear cells (PBMC) obtained from a host immunized as discussed above. For example, PBMC can be separated by using Lymphocyte Separation Medium gradient (Organon Teknika, Durham, N.C., USA) as previously described [Boyum et al, *Scand J. Clin Lab Invest* 21:77-80 (1968)]. Washed PBMC are resuspended in a complete medium, for example, RPMI 1640 (GIBCO) supplemented with 10% pool human AB serum (Pel-Freeze Clinical System, Brown Dear, Wis., USA), 2 mM glutamine, 100 U/ml penicillin and 100 μg/ml of streptomycin (GIBCO). PBMC at a concentration of about $2\times10^5$ cells in complete medium in a volume of, for example 100 μl are added into each well of a 96-well flat-bottom assay plate (Costar, Cambridge, Mass., USA). The antigen or peptides are added into the cultures in a final concentration of about 50 μg/ml and incubated at 37° C. in a humidified atmosphere containing 5% $CO_2$ for 5 days. After removal of peptide containing media, the cultures are provided with fresh human IL-2 (10 U/ml) after 5 days and replenished with IL-2 containing medium every 3 days. Primary cultures are restimulated with the same peptide (50 μg/ml) on day 16. $5\times10^5$ irradiated (4,000 rad) autologous PBMC are added in a volume of about 50 μl complete medium as antigen-presenting cells (APC). About five days later, the cultures are provided with human IL-2 containing medium as described previously. Cells are restimulated for 5 days at intervals of 16 days.

Epitope Mapping

The cytotoxic T-cells of the present invention can be used to determine the epitope of the PSA that elicits a cytotoxic T-cell. For example, one can cut the PSA into numerous peptide fragments. Alternatively, the fragments can be chemically synthesized. Cytotoxic T-cells can then be plated and different fragments added to different wells. Only T-cells which recognize one of the pre-selected peptide fragments as an epitope will continue to expand, thereby permitting ready identification.

These fragments can then be used to elicit cytotoxic T-cell instead of using the whole protein. Additionally, one can prepare other fragments containing the epitope to enhance its ability to elicit a cytotoxic T-cell response. Modifications to these fragments are well known in the art and include the use of conjugates, specific amino acid residues such as cystines, etc.

Drug Assay

The cytotoxic T-cell can also be used to screen for compounds which enhance the ability of the antigen to create a cytotoxic T-cell response. For example, cytotoxic T-cells can be incubated with a selected epitope, for example, in a microtiter plate. The compound to be tested, e.g. a drug, is then added to the well and the growth of the T-cells is measured. T-cell expansion indicates that the test compound enhances the T-cell response. Such compounds can be further evaluated.

Therapy

The cytotoxic T-cell can be cultured to amplify its number and then injected back into the host by a variety of means. Generally, between $1\times10^5$ and 2×10" cytotoxic T-cells per infusion are administered in, for example, one to three infusions of 200 to 250 ml each over a period of 30 to 60 minutes. After the completion of the infusions, the patient may be treated with recombinant interleukin-2 with a dose of 720,000 IU per kilogram of body weight intravenously every eight hours; some doses can be omitted depending on the patient's tolerance for the drug. In addition, after infusion, additional antigen or fragments containing T-cell eliciting epitope(s) may be administered to the patient to further expand the T-cell number. The antigen or epitope may be formulated with an adjuvant and/or may be in a liposomal formulation.

The cytotoxic T-cells can also be modified by introduction of a viral vector containing a DNA encoding TNF and reintroduced into a host in an effort to enhance the anti-tumor activity of the cells. Other cytokines can also be used.

The recombinant vector can be administered using any acceptable route, including, for example, scarification and injection, e.g. intradermal, subcutaneous, intramuscular, intravenous or intraperitoneal.

For parenteral administration, the recombinant vectors will typically be injected in a sterile aqueous or non-aqueous solution, suspension or emulsion in association with a pharmaceutically-acceptable carrier such as physiological saline.

Reference Example 1

Construction of Vectors

Pox Viruses

A number of pox viruses have been developed as live viral vectors for the expression of heterologous proteins (Cepko et al, *Cell* 37:1053-1062 (1984); Morin et al, *Proc. Natl. Acad. Sci. USA* 84:4626-4630 (1987); Lowe et al, *Proc. Natl. Acad. Sci. USA,* 84:3896-3900 (1987); Panicali & Paoletti, *Proc. Natl. Acad. Sci. USA,* 79:4927-4931 (1982); Mackett et al, *Proc. Natl. Acad. Sci. USA.* 79:7415-7419 (1982)). Representative fowlpox and swinepox virus are available through the ATCC under accession numbers VR-229 and VR-363, respectively.

DNA Vectors For In Vivo Recombination With A Parent Virus Genes that code for desired carcinoma associated antigens are inserted into the genome of a pox virus in such a manner as to allow them to be expressed by that virus along with the expression of the normal complement of parent virus proteins. This can be accomplished by first constructing a DNA donor vector for in vivo recombination with a pox virus.

In general, the DNA donor vector contains the following elements:

(i) a prokaryotic origin of replication, so that the vector may be amplified in a prokaryotic host;

(ii) a gene encoding a marker which allows selection of prokaryotic host cells that contain the vector (e.g. a gene encoding antibiotic resistance);

(iii) at least one gene encoding a desired protein located adjacent to a transcriptional promoter capable of directing the expression of the gene; and (iv) DNA sequences homologous to the region of the parent virus genome where the foreign gene(s) will be inserted, flanking the construct of element (iii).

Methods for constructing donor plasmids for the introduction of multiple foreign genes into pox virus are described in WO91/19803, the techniques of which are incorporated herein by reference. In general, all DNA fragments for construction of the donor vector, including fragments containing transcriptional promoters and fragments containing sequences homologous to the region of the parent virus genome into which foreign genes are to be inserted, can be obtained from genomic DNA or cloned DNA fragments. The donor plasmids can be mono-, di-, or multivalent (i.e. can contain one or more inserted foreign gene sequences).

The donor vector preferably contains an additional gene which encodes a marker which will allow identification of recombinant viruses containing inserted foreign DNA. Several types of marker genes can be used to permit the identification and isolation of recombinant viruses. These include genes that encode antibiotic or chemical resistance (e.g. see Syropoulos et al, *J. Virol.*, 62:1046 (1988); Falkner and Moss, *J. Virol.*, 62:1849 (1988); Franke et al, *Mol. Cell. Biol.*, 5:1918 (1985), as well as genes such as the *E. coli* lacZ gene, that permit identification of recombinant viral plaques by calorimetric assay (Panicali et al, *Gene*, 47:193-199 (1986)).

Integration of Foreign DNA Sequences Into the Viral Genome And Isolation Of Recombinants Homologous recombination between donor plasmid DNA and viral DNA in an infected cell results in the formation of recombinant viruses that incorporate the desired elements. Appropriate host cells for in vivo recombination are generally eukaryotic cells that can be infected by the virus and transfected by the plasmid vector. Examples of such cells suitable for use with a pox virus are chick embryo fibroblasts, HuTK143 (human) cells, and CV-1, Vero and BSC-40 (monkey) cells. Infection of cells with pox virus and transfection of these cells with plasmid vectors is accomplished by techniques standard in the art (Panicali and Paoletti, U.S. Pat. No. 4,603,112, WO89/03429).

Following in vivo recombination, recombinant viral progeny can be identified by one of several techniques. For example, if the DNA donor vector is designed to insert foreign genes into the parent virus thymidine kinase (TK) gene, viruses containing integrated DNA will be TK- and can be selected on this basis (Mackette et al, *Proc. Natl. Acad. Sci. USA* 79:7415 (1982)). Alternatively, co-integration of a gene encoding a marker or indicator gene with the foreign gene(s) of interest, as described above, can be used to identify recombinant progeny. One preferred indicator gene is the *E. coli* lacZ gene: recombinant viruses expressing ß-galactosidase can be selected using a chromogenic substrate for the enzyme (Panicali et al, *Gene*, 47:193 (1986)).

Characterizing The Viral Antigens Expressed by Recombinant Viruses

Once a recombinant virus has been identified, a variety of methods can be used to assay the expression of the polypeptide encoded by the inserted gene. These methods include black plaque assay (an in situ enzyme immunoassay performed on viral plaques), Western blot analysis, radioimmunoprecipitation (RIPA), and enzyme immunoassay (EIA).

Example I

Generation of PSA Specific Immune Response

Materials and Methods

Recombinant Vaccinia Virus

A 786 bp DNA fragment encoding the entire open reading frame of human prostate specific antigen was amplified by reverse transcriptase PCR (GeneAmp RNA PCR Kit, Perkin Elmer, Norwalk, Conn.) from total RNA extracted from the human metastatic prostate adenocarcinoma cell line, LNCaP.FGC (CRL 1740, American Type Culture Collection (ATCC), Rockville, Md.). The predicted amino acid sequence derived from the PSA coding sequence was shown to be nearly identical to the published sequence (Lundwall et al, 1987), differing only in a change from asparagine to tyrosine at position 220. The PSA DNA fragment, containing the entire coding sequence for PSA, 41 nucleotides of the 5' untranslated region, and 520 nucleotides of the 3' untranslated region, was inserted into the Xba 1 restriction endonuclease cleavage site of the vaccinia virus transfer vector pT116. The resulting plasmid, designated pT1001, contains the PSA gene under the control of the vaccinia virus 40 K promoter (Gritz et al 1990) and the *E. coli* lacZ gene under the control of the fowlpox virus C1 promoter (Jenkins et al, 1991). The foreign genes are flanked by DNA sequences from the Hind III M region of the vaccinia genome. A plaque-purified isolate from the Wyeth (New York City Board of Health) strain of vaccinia was used as the parental virus in the construction of the recombinant vaccinia virus. The generation of recombinant vaccinia virus was accomplished via homologous recombination between vaccinia sequences in the Wyeth vaccinia genome and the corresponding sequences in pT1001 in vaccinia-infected $RK_{13}$ cells (CCL 37, ATCC) transfected with pT1001. Other cell lines for generation of the recombinant include but are not limited to CV-1 and Vero. Recombinant virus was identified using a chromogenic assay, performed on viral plaques in situ, that detects expression of the lacZ gene product in the presence of halogenated indolyl-beta-D-galactoside (Bluo-gal), as described previously (Panicali et al, 1986). Appropriate blue recombinant viruses were purified by four rounds of plaque-purification. Virus stocks were prepared by clarifying infected $RK_{13}$ cell lysates followed by centrifugation through a 36% sucrose cushion.

Characterization of Recombinant Virus

Southern Analysis of DNA Recombination

The recombinant vaccinia genome was analyzed by viral DNA extraction, restriction endonuclease digestion with Hind III and Southern blotting as previously described (Kaufman et al, 1991).

Western Analysis of Protein Expression

Confluent BSC-40 cells were infected with either parental wild type vaccinia virus (designated V-Wyeth) or recombinant vaccinia-PSA (designated rV-PSA) at an MOI of 1 in Dulbecco's Modified Eagle's Medium containing 2% fetal bovine serum. After an overnight infection, the medium was removed from the cells, and an aliquot was methanol precipitated to assay for the presence of secreted PSA. The infected cells were lysed in hypotonic lysis buffer (150 mM NaCl, 0.05% EDTA, 10 mM KCl, 1 mM PMSF) and then sonicated. Cell lysates and culture media were electrophoresed on an SDS-10% acrylamide gel. The proteins were transblotted to nitrocellulose and the blot was incubated with a rabbit antibody specific for PSA (P0798, Sigma Chemical Co., St. Louis, Mo.) for 4 hours at ambient temperature, washed and then incubated with goat anti-rabbit phosphatase-labeled secondary antibody (AP, Kirkegaard & Perry Laboratories, Gaithersburg, Md.) and developed according to the manufacture's instructions.

Generation of B-Cell Lines

Monkey autologous B lymphoblastoid cell lines (BLCL) were established by infecting $1 \times 10^5$ freshly isolated PBMCs in 100 ml of RPMI 1640 supplemented with L-glutamine, gentamicin, and 10% FCS (Biofluids, Rockville, Md.) with 100 ml supernatant from S594 cells (kindly provided by Dr. M. D. Miller, Harvard Medical School, New England Regional Primate Research Center, Southborough, Mass.) which contains the baboon herpesvirus *Herpes papio*, in a 96 well, flat-bottomed plate (Costar, Cambridge, Mass.). Following transformation, cells were expanded and media changed once weekly.

Immunization of Monkeys

Twelve juvenile male rhesus monkeys (*Macaca mulatta*), ages 1 to 2 years, were assigned to three vaccination groups of four animals each. One animal from each group was prostatectomized. Animals were immunized 3 times on days 1, 29 and 57. Doses of either $1 \times 10^7$ or $1 \times 10^8$ PFU of rV-PSA were administered to 4 animals by skin scarification. V-Wyeth ($1 \times 10^8$ PFU) was administered to 4 animals as controls. The animals were housed and maintained at the Toxicology Research Laboratory, University of Illinois at Chicago (TRL/UIC) in accordance with the guidelines of the National Cancer Institute Animal Care and Use Committee and the Guide for the Care and Use of Laboratory Animals (Department of Health and Human Services Publication NIH 85-23, revised 1985 by the FDA Center for Biologics Evaluation and Research Office of Biological Product Review, Division of Product Quality Control, Pathology and Primatology Laboratory, Bethesda, Md.).

Toxicology

Physical examinations were performed on ketamine (Ketamine® HCl, 10 mg/kg I.M.) sedated animals. Rectal temperatures and weights were recorded for each monkey on a weekly basis. The vaccination site was observed and erythema and swelling were measured by caliper. Each animal was examined for regional lymphadenopathy, hepatomegaly, and splenomegaly. Any other gross abnormalities were also recorded.

Blood was obtained by venipuncture from the femoral vein of ketamine sedated animals before and after each immunization. A complete blood count, differential hepatic and renal chemistry evaluation was performed on each monkey by TRL/UIC. Results were compared to normal primate values (Kantor et al., 1992b). Circulating levels of PSA before and after immunization were analyzed by radioimmunoassay (Tandem™, Hybritech, San Diego, Calif.).

Measurement of Antibody Titers

Prior to each immunization and 2 weeks following each immunization, anti-PSA antibody was quantified by ELISA. Microtiter plates were coated with purified PSA (100 ng/well, Calbiochem, La Jolla, Calif.), ovalbumin (100 ng/well, Sigma), or $1 \times 10^7$ PFU/well UV-inactivated V-Wyeth in PBS. The plates were blocked with 2% BSA in PBS, dried and stored at −20° C. until used. The plates were incubated with serum diluted 1:5, as well as a monoclonal antibody for PSA (DAKO M750, Denmark) as a standard control, for 24 hours at 4° C. Plates were washed several times with PBS containing 1% BSA, and incubated at 37° C. for 45 min with horseradish peroxidase-conjugated goat anti-human IgG or IgM heavy chain specific antiserum (1:8000) (Southern Biotechnology Associates, Birmingham, Ala.) and antibody detected by HRP substrate system (Kirkegaard & Perry Laboratories, Gaithersburg, Md.) according to the manufacture's instructions. The absorbance of each well was read at 405 nm using a Bio-Tek EL310 microplate ELISA reader (Winooski, Vt.).

Lymphoproliferative Assay

Autologous monkey BLCL were plated at a density of $3 \times 10^6$ cells/wells in 24 well plates with 160 mg/well purified PSA (Fitzgerald, Concord, Mass.) or 160 mg/well ovalbumin (Sigma) a 37° C. for 24 hours. Cells were then γ-irradiated (14000 rad), harvested, washed and suspended at a final concentration of $1 \times 10^7$/ml. Fresh monkey PBMCs from heparinized blood, 6 weeks to 7 months after the last immunization, were isolated on lymphocyte separation medium (Organon Teknika, West Chester, Pa.). Lymphoproliferative responses were evaluated by co-culturing $1.5 \times 10^5$ cells with $5 \times 10^5$ cells/well of autologous BLCL in 0.2 ml of RMPI 1640 supplemented with 10% heat-inactivated fetal calf serum in flat-bottomed 96 well plates (Costar) for 5 days. PBMCs were cultured with $2 \times 10^7$ PFU/ml UV-irradiated V-Wyeth as a recall antigen or 2 mg/ml Con-A as positive controls. Cells were labeled for the final 12-18 h of the incubation with 1 mCi/well [$^3$H]thymidine (New England Nuclear, Wilmington, Del.) and harvested with a PHD cell harvester (Cambridge Technology, Cambridge, Mass.). The incorporated radioactivity was measured by liquid scintillation counting (LS 6000IC; Beckman, Duarte, Calif.). The results from triplicate wells were averaged and are reported as mean±SEM.

Results

Generation and Characterization of Recombinant Virus

The cDNA fragment encoding the open reading frame of human PSA was obtained by reverse transcriptase PCR using PSA specific oligonucleotide primers 5' TCTAGAAGC-CCCAAGCTTACCACCTGCA 3' (SEQ. ID. NO.: 16), 5' TCTAGATCAGGGGTTGGCCACGATGGT-GTCCTTGATCCACT 3' (SEQ. ID. NO.: 17), and ligated into the vaccinia virus transfer vector pT106. This vector contains a strong vaccinia virus early/late promoter (designated P40) upstream of the multiple cloning sited to drive the synthesis of the inserted gene product. The ligation and orientation of the PSA DNA fragment, as well as promoter position were verified by PCR and sequencing. The chimeric vector construct was inserted into the vaccine virus genome Hind III M site by homologous recombination as previously reported (Kaufman, et al., (1991)), and confirmed by Southern analysis probing with $^{32}$P radiolabeled DNA corresponding to PSA sequences and vaccinia sequences in the Hind III M region (data not shown). The entire cDNA sequence of PSA in the vaccinia virus clone was shown to be nearly identical to the published sequences (Lundwall, et al., 1987).

Expression of recombinant protein was confirmed by western blot analysis of supernatant fluids and protein extracts from rV-PSA infected BSC-40 cells. These cells are routinely used for the evaluation of recombinant vaccinia products (Moss, et al., 1993). Incubation of cell supernatant blots from rV-PSA infected cells with rabbit anti-PSA antibody revealed a single immunoreactive polypeptide of approximately 33,000 daltons (FIG. 1, lanes 2-4). Similarly, incubation of protein extract blots from rV-PSA infected cells revealed a single band of the same molecular weight (FIG. 1, lanes 7-9).

This is consistent with the predicted size of the PSA molecule (Armbruster, et al., 1993; Wang, et al., 1982). Cell supernatant blots (lane 1) or protein extract blots (lane 6) from cells infected with parental strain V-Wyeth remained negative for expression of PSA. These results thus demonstrate that a recombinant vaccinia virus can faithfully express the human PSA gene product.

Rhesus Monkey Model

The prostate gland of the rhesus monkey is structurally and functionally similar to the human prostate (Wakui, et al., 1992). At the molecular level, there is 94% homology between both the amino acid and nucleic acid sequences of rhesus PSA (Gauthier, et al., 1993) and human prostate specific antigen (Kerr, et al., 1995; Lundwall, et al., 1987). Human PSA is essentially an autoantigen in the rhesus monkey.

Experimental Design

Table 1 delineates the protocol used in the immunization of 12 rhesus monkeys with either rV-PSA or the control V-Wyeth by skin scarification.

Three groups of 4 animals were immunized with either rV-PSA at $1 \times 10^7$ PFU/dose, rV-PSA at $1 \times 10^8$ PFU/dose, or V-Wyeth at $10^8$ PFU/dose 3 times at 4 week intervals. These doses were chosen to ascertain the maximum tolerated dose for safety as well as to obtain maximum humoral and cell-mediated responses to PSA.

The rhesus monkeys were divided into 3 groups: high dose V-Wyeth, low dose rV-PSA, and high-dose rV-PSA. One animal in each group was surgically prostatectomized to parallel two situations with regard to potential therapy in humans: (a) prostate intact, with primary and/or metastatic disease; or (b) patients prostatectomized with prostate cancer metastatic deposits. The presence of an intact prostate gland could conceivably serve as an antigen 'sink', either inducing energy through persistence of antigen, or masking immunological effects by sequestering reactive cells or antibodies.

Physical Consequence of Immunization

Figure 2A:
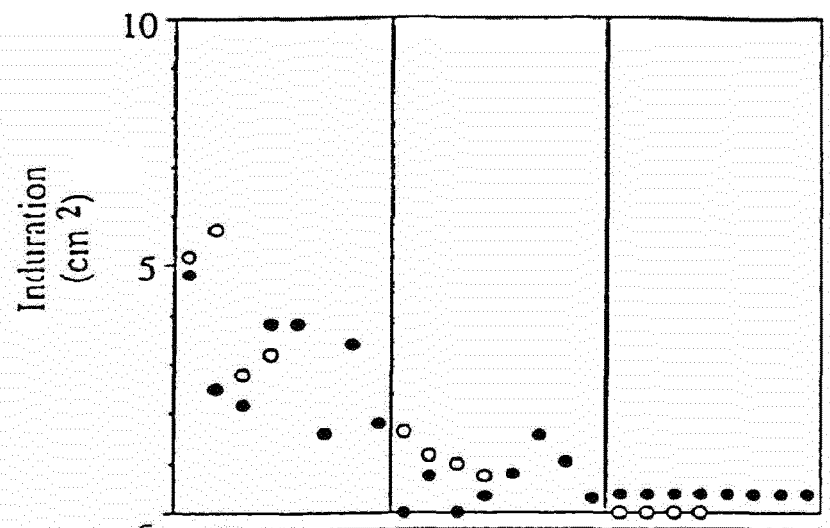
FIGS. 2A, 2B and 2C show the manifestation of rV-PSA immunization.
Figure 2B:
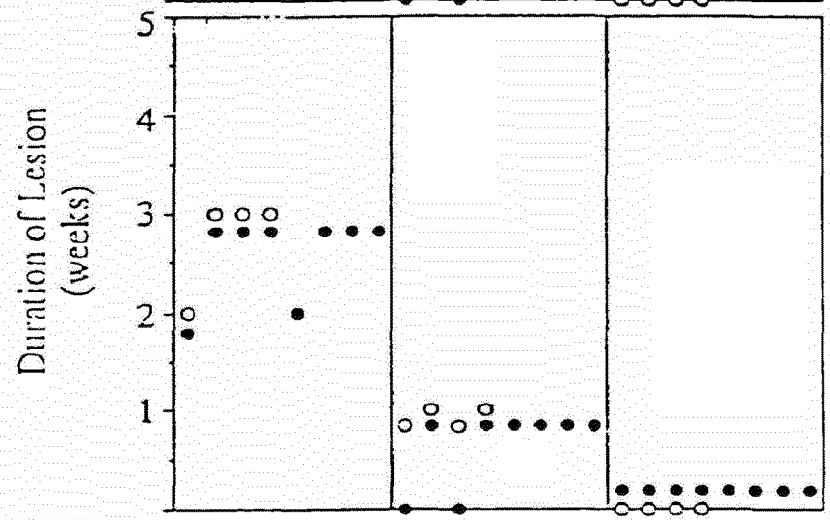
Figure 2C:
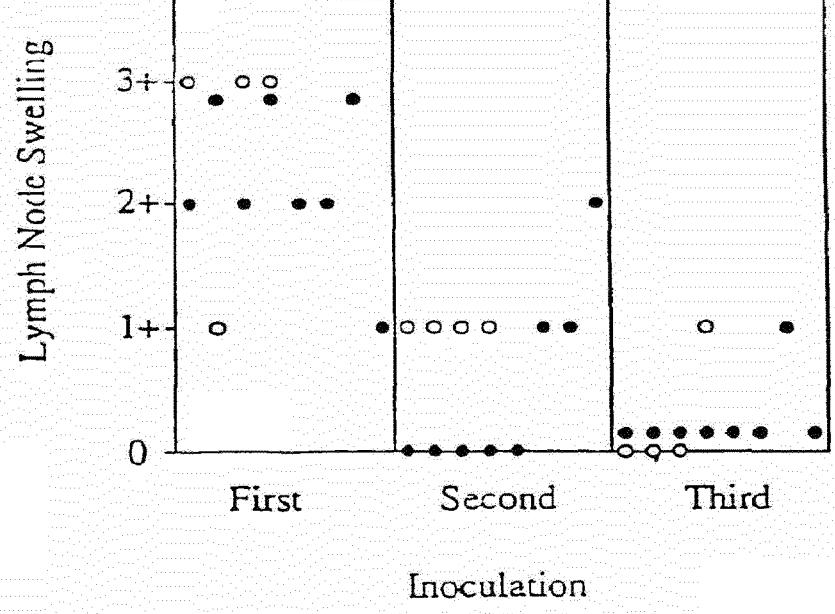

The area of the lesions induced by rV-PSA or V-Wyeth was analyzed 7 days following each inoculation. In general, more induration was seen after the first inoculation, compared to the second inoculation (FIG. 2A). After the third inoculation, there was no swelling of the vaccination site. The duration of the lesion following each immunization was shorter after each inoculation (FIG. 2B). Regional lymph node swelling following vaccination was greater in most monkeys following the first immunization, compared to the second, or third immunization (FIG. 2C). In general, no differences were seen in these parameters with the use of rV-PSA or V-Wyeth. Monkeys receiving V-Wyeth were compared with those receiving rV-PSA with respect to constitutional symptoms. Mild temperature elevations were seen in all animals following vaccination. There was no evidence of weight loss, hepatomegaly or splenomegaly in any of the animals, and there was no differences between V-Wyeth or rV-PSA treated animals (data not shown). Animals were tested for complete blood count, differential, and hepatic and renal chemistries. Complete blood counts remained within normal limits throughout the study in both V-Wyeth and rV-PSA immunized animals (Table 2). Hepatic and renal functions were assessed prior to immunization and 12 weeks following primary immunization (Table 3). Parameters analyzed included alkaline phosphatase, blood urea nitrogen, alanine aminotransferase, aspartate aminotransferase, lactate dehydrogenase, and creatine and creatine kinase levels. There was no significant difference between animals receiving V-Wyeth or rV-PSA. There was no detectable PSA in the circulation of any of these monkeys after any immunization (detection limit was 0.1 ng/ml). At this time, which is 54 weeks post all immunizations, no toxicities were observed in monkeys of any of the groups, including those which were prostatectomized.

PSA Specific Humoral Responses

As indicated in Table 1, monkeys 1-4 were administered V-Wyeth while monkeys 5-12 were administered rV-PSA. Sera from each of these monkeys were analyzed by ELISA for immunoreactivity to PSA or UV-inactivated V-Wyeth, and ovalbumin as control antigen. Sera obtained from monkeys prior to vaccination were negative for reactivity to PSA (Table 4, PI). Fifteen days following primary immunization, monkeys in both the $1 \times 10^8$ and $1 \times 10^7$ dose rV-PSA groups developed low titer IgM antibodies specific for PSA (titers were determined at a 1:5 serum dilution). Although other isotypes of antibody were analyzed (IgG, IgA, IgM), only IgM was induced by rV-PSA throughout the observation period of 270 days. The antibody titers decreased over the 4 weeks prior to the next inoculation. Prior to the second vaccination on day 29, 3 of 4 animals in the $1 \times 10^7$ rV-PSA group remained positive for PSA antibody, while 4 of 4 animals remained positive in the $1 \times 10^8$ rV-PSA group. Anti-PSA antibody titers increased after the second vaccination on day 29, but remained static after the third vaccination on day 57. By 270 days after the primary immunization, all animals were negative for PSA IgM antibody. Monkeys remained negative for IgG specific for PSA throughout the observation period (data not shown). There was no correlation between rV-PSA dose and anti-PSA IgM titer, nor was there any apparent effect of prostatectomy. All monkey sera were negative for IgG or IgM to ovalbumin at all time points; as a positive control, however, the IgG titer in all three treatment groups to vaccinia virus was greater than 1:2000 as early as 29 days after the primary immunization (data not shown).

In general, vaccinia virus is a weak human pathogen (Paoletti et al., 1993). Following vaccination, local erythema, induration, low-grade fever, and regional lymphadenopathy are common. The virus replicates in the epidermal cells of the skin and the virus is usually cleared within 14 days. All monkeys, whether given V-Wyeth or rV-PSA, exhibited the usual low grade constitutional symptoms of a vaccinia virus infection (FIG. 2). There was no evidence of any adverse effects as indicated by changes in blood counts, differentials, hepatic and renal chemistries (Tables 2-3). The monkeys appeared healthy, without any physical signs of toxicity, throughout the 54 weeks of observation.

Although the rV-PSA construct was unable to elicit an anti-PSA IgG response, PSA specific IgM responses were noted in all rV-PSA immunized monkeys regardless of dose level (Table 4). These antibody responses were of low titer, short lived and could not be boosted, indicating induction of a primary response but not memory B-cells or affinity maturation.

PSA Specific Lymphoproliferative Assay

PSA specific T-cell responses in monkeys immunized with rV-PSA or V-Wyeth were analyzed using a lymphoproliferative assay. As seen in Table 5, the PBMCs from all monkeys analyzed responded, regardless of whether they received rV-PSA or V-Wyeth, to the lymphocyte mitogen concanavalin-A, as well as with the recall antigen UV-inactivated V-Wyeth. Differential responses to PSA versus medium alone or ovalbumin were seen in 1 animal (number 6) in the $1 \times 10^7$ PFU rV-PSA group. All PBMCs from animals in the $1 \times 10^8$ PFU rV-PSA group, however, responded to PSA in this assay. This experiment was repeated 5 times with similar results and data shown in Table 5 is from PBMCs isolated from monkeys 270 days after the primary immunization. No differences in PSA specific T-cell responses were seen in the prostatectomized monkeys.

To investigate cell mediated responses to the administration of rV-PSA, lymphoproliferative assays were performed using PBMCs from animals receiving the recombinant vaccine. One of four monkeys receiving the lower dose of rV-PSA ($1 \times 10^7$ PFU) and four of four receiving the higher dose ($1 \times 10^8$ PFU) maintained specific T-cell responses to PSA protein up to 270 days following primary immunization as indicated by the lymphoproliferative assay (Table 5). Prostatectomy appeared to have no effect on either the humoral or cellular responses of monkeys receiving rV-PSA. Evidence of PSA specific T-cell responses in monkeys lacking mature antibody isotypes could be due to two distinct events following vaccination with rV-PSA: a T-cell independent event, leading to IgM production, and a T-cell dependent event, leading to specific lymphoproliferative responses.

TABLE 1

Inoculation protocol of rhesus monkeys with the PSA recombinant and wild-type vaccinia virus

| Monkey | Prostate | Immunogen | Dose* (PFU) |
|---|---|---|---|
| 1 | Yes | V-Wyeth | $1 \times 10^8$ |
| 2 | Yes | V-Wyeth | $1 \times 10^8$ |
| 3 | Yes | V-Wyeth | $1 \times 10^8$ |
| 4 | No | V-Wyeth | $1 \times 10^8$ |
| 5 | Yes | rV-PSA | $1 \times 10^7$ |
| 6 | Yes | rV-PSA | $1 \times 10^7$ |
| 7 | Yes | rV-PSA | $1 \times 10^7$ |
| 8 | No | rV-PSA | $1 \times 10^7$ |
| 9 | Yes | rV-PSA | $1 \times 10^8$ |
| 10 | Yes | rV-PSA | $1 \times 10^8$ |
| 11 | Yes | rV-PSA | $1 \times 10^8$ |
| 12 | No | rV-PSA | $1 \times 10^8$ |

*All animals received 3 immunizations at 4 week intervals.

TABLE 2

Mean WBC count, hematocrit, and differential count in rhesus monkeys receiving recombinant or wild-type vaccine

| | | V-Wyeth (n = 4) | | rV-PSA (n = 8) | |
|---|---|---|---|---|---|
| Test | Normal ranges | Before immunization[a] | After immunization[b] | Before immunization | After immunization |
| WBC | $7\text{-}15 \times 10^3$ | 5.0 ± 0.8 | 5.1 ± 0.5 | 5.2 ± 0.7 | 5.8 ± 0.9 |
| Hematocrit (vol. %) | 33-43 | 37.4 ± 0.2 | 37.0 ± 0.1 | 37.8 ± 0.4 | 37.0 ± 0.5 |
| Lymphocytes | $1\text{-}7 \times 10^3$ | 2.8 ± 0.7 | 3.9 ± 0.5 | 2.2 ± 0.4 | 3.5 ± 0.8 |
| SEGS[c] (%) | 3-69 | 2.0 ± 0.2 | 0.78 ± 0.2 | 2.9 ± 0.6 | 1.9 ± 0.3 |
| Monocytes (%) | 0-8 | 0.1 ± 0.05 | 0.2 ± 0.04 | 0.1 ± 0.04 | 0.2 ± 0.50 |
| Eosinophils (%) | 0-8 | 0.1 ± 0.02 | 0.2 ± 0.10 | 0.1 ± 0.03 | 0.1 ± 0.02 |

[a] 1 week prior to primary immunization
[b] 12 weeks following primary immunization
[c] Segmented lymphocytes

TABLE 3

Mean serum chemistry values in rhesus monkeys receiving recombinant or wild-type vaccine.

| | | V-Wyeth (n = 4) | | rV-PSA (n = 8) | |
|---|---|---|---|---|---|
| Test | Normal ranges | Before immunization[a] | After immunization[b] | Before immunization | After immunization |
| ALKP[c] (u/l) | 200-800 | 451 ± 48 | 610 ± 33 | 339 ± 74 | 454 ± 47 |
| BUN[d] (mg/dl) | 12-30 | 19.0 ± 3.0 | 17.8 ± 0.9 | 17.1 ± 0.6 | 20.5 ± 1.0 |
| ALT[e] (u/l) | 20-60 | 25.2 ± 1.9 | 22.8 ± 1.0 | 28.9 ± 5.3 | 25.8 ± 1.6 |
| AST[f] (u/l) | 40-80 | 37.8 ± 2.3 | 31.8 ± 4.4 | 37.9 ± 3.6 | 31.9 ± 2.4 |
| LDH[g] (u/l) | 200-500 | 194 ± 20 | 212 ± 21 | 236 ± 41 | 194 ± 13 |
| Creatine (mg/dl) | 0.5 ± 1.0 | 0.9 ± 0.10 | 0.8 ± 0.03 | 0.8 ± 0.05 | 0.8 ± 0.02 |
| Creatine Kinase (u/l) | 500-2000 | 662 ± 112 | 466 ± 119 | 498 ± 120 | 563 ± 81 |

[a] 1 week prior to primary immunization
[b] 12 weeks following primary immunization
[c] Alkaline phosphatase
[d] Blood urea nitrogen
[e] Alanine aminotransferase
[f] Asparate aminotransferase
[g] Lactate dehydrogenase

TABLE 4

Primate IgM[a] Response to Inoculation with rV-PSA

| Monkey | Immunogen | Dose (PFU) | PI[d] | 18 | 29[e] | 43 | 57[e] | 71 | 270 |
|---|---|---|---|---|---|---|---|---|---|
| 1 | V-Wyeth | 1 × 10⁸ | ND[f] | ND | ND | ND | ND | ND | ND |
| 2 | V-Wyeth | 1 × 10⁸ | ND | ND | ND | ND | ND | ND | ND |
| 3 | V-Wyeth | 1 × 10⁸ | ND | ND | ND | ND | ND | ND | ND |
| 4[c] | V-Wyeth | 1 × 10⁸ | ND | ND | ND | ND | ND | ND | ND |
| 5 | rV-PSA | 1 × 10⁷ | ND | >40 | 5 | 20 | >40 | >40 | ND |
| 6 | rV-PSA | 1 × 10⁷ | ND | >40 | ND | ND | 20 | 20 | ND |
| 7 | rV-PSA | 1 × 10⁷ | ND | >40 | 5 | 20 | 20 | 20 | ND |
| 8[c] | rV-PSA | 1 × 10⁷ | ND | >40 | 5 | 10 | >40 | >40 | ND |
| 9 | rV-PSA | 1 × 10⁸ | ND | 20 | 5 | 20 | 10 | 10 | ND |
| 10 | rV-PSA | 1 × 10⁸ | ND | 20 | 5 | 40 | >40 | NT[g] | ND |
| 11 | rV-PSA | 1 × 10⁸ | ND | >40 | >40 | >40 | >40 | >40 | ND |
| 12[c] | rV-PSA | 1 × 10⁸ | ND | >40 | 20 | 40 | 20 | 20 | ND |

[a]All monkeys seras were negative for IgG to PSA at all time points; All seras were positive for IgG to vaccinia virus (>1:2000) at day 71.
[b]Monkeys received vaccinations on days 1, 29 and 57. Sera (1:5) was tested by ELISA. Titers were calculated using an O.D. of 0.4.
[c]Animal was prostatectomized.
[d]PI, Pre-immune.
[e]Animals bled before boosting.
[f]ND, not detectable; limit of detection was <1:5 dilution.
[g]NT, not tested.

TABLE 5

PSA Specific Lymphoproliferative T-cell Responses of Rhesus PBMCs 270 Days Following Inoculation with rV-PSA

| Monkey | Immunogen | Dose (PFU) | Medium | Con A | Oval | UV-Wyeth | PSA[d] |
|---|---|---|---|---|---|---|---|
| 1 | V-Wyeth | 1 × 10⁸ | 397 | 65701 | 376 | 24785 | 414 |
| 2[b] | V-Wyeth | 1 × 10⁸ | NT | NT | NT | NT | NT |
| 3 | V-Wyeth | 1 × 10⁸ | 450 | 84860 | 522 | 18859 | 413 |
| 4[c] | V-Wyeth | 1 × 10⁸ | 532 | 107840 | 553 | 16571 | 387 |
| 5 | rV-PSA | 1 × 10⁷ | 412 | 85276 | 408 | 6040 | 539 |
| 6 | rV-PSA | 1 × 10⁷ | 401 | 96368 | 404 | 7776 | 3,134 |
| 7 | rV-PSA | 1 × 10⁷ | 417 | 90801 | 522 | 10908 | 434 |
| 8[c] | rV-PSA | 1 × 10⁷ | 1069 | 99216 | 744 | 15346 | 484 |
| 9 | rV-PSA | 1 × 10⁸ | 384 | 106248 | 386 | 14499 | 10,635 |
| 10 | rV-PSA | 1 × 10⁸ | 432 | 92263 | 404 | 19872 | 18,561 |
| 11 | rV-PSA | 1 × 10⁸ | 411 | 94055 | 1063 | 5124 | 16,245 |
| 12[c] | rV-PSA | 1 × 10⁸ | 420 | 124896 | 392 | 11944 | 12,945 |

[a]Antigen concentrations were: Con a (2 µg/ml); Ovalbumin (100 µg/ml); UV Wyeth (2 × 10⁷ pfu/ml); and PSA (100 µg/ml). Each value represents a mean CPM of triplicate samples. Standard deviation never exceeded 10%.
[b]NT, not tested. B-cells were not transformed for this animal.
[c]Animal was prostatectomized.
[d]Values in bold are significant when compared to their respective medium control values (p < 0.001).

Example II

Identification of Potential Prostate Specific Antigen (PSA) Specific T Cell Epitopes Since the entire amino acid sequence of human PSA is known and human class 1 HLA A2 consensus motifs have been described, studies were undertaken to identify a series of peptides that would potentially bind class 1 A2 molecules. A2 was chosen since it is most common HLA class 1 molecule being represented in approximately 50% of North American Caucasians and 34% of African Americans. The peptide sequence of PSA was thus examined for matches to the consensus motifs for HLA A2 binding peptides. Peptides were only selected if their sequence diverged sufficiently from the PSA-related human glandular kallikrein (HGK) gene and pancreatic kallikrein antigen (PKA) sequences.

The amino acid sequence of human PSA was scanned using a predictive algorithm that combines a search for anchor residues with numerical assignments to all residues at all positions. The T2 cell binding assay was then used to determine which peptides bound human HLA A2 molecules. As can be seen in Table 6, PSA peptides 141-150, 154-163 and 146-154 scored positive in this assay (Nijman, H. W., et al., Eur. J. Immunol. 23:1215-1219, 1993). Table 7 gives the amino acid sequence of these peptides and compares them to corresponding sequences of HGK and PKA.

TABLE 6

PSA peptide binding assay

| Antigen | MAb A2, 69 |
|---|---|
| None | 127.25[a] |
| PSA 141-150 | 230.34 |
| PSA 146-154 | 223.97 |
| PSA 154-163 | 182.30 |

Peptides were used at a concentration of 50 µg/ml
[a]Mean channel fluorescent intensity.
CIRA2 cell line was used as positive control for anti-A2 staining [(241.15)].

TABLE 7

| | | PSA peptide amino acid sequence | |
|---|---|---|---|
| PSA | 141-150 | F L T P K K L Q C V | (Seq.ID No. 1) |
| HGK | | – – R – R S – – – – | (Seq.ID No. 7) |
| PKA | | – S F – D D – – – – | (Seq.ID No. 8) |
| PSA | 146-154 | K L Q C V D L H V | (Seq.ID No. 9) |
| HGK | | S – – – – S – – L | (Seq.ID No. 10) |
| PKA | | D – – – – – – K I | (Seq.ID No. 11) |
| PSA | 154-163 | V I S N D V C A Q V | (Seq.ID No. 2) |
| HGK | | L L – – – M – – R A | (Seq.ID No. 12) |
| PKA | | I L P – – E – E K A | (Seq.ID No. 13) |

Example III

Establishment of Human T Cell Lines Cytolytic for Human Tumor Cells Expressing PSA PBMC from normal healthy donors expressing the HLA A2 class 1 allele were used in an attempt to determine if PSA specific peptides are immunogenic for humans. Peptides 141-150 and 154-163 were used in this study.

The methodology used for the establishment of these cell lines involves pulsing of PBMC with peptide and IL-2 as previously described (Tsang, K. Y., et al, 1995, *J. Nat'l Cancer Inst.*, Vol. 87(13):982-90 and in U.S. application Ser. No. 08/396,385, the disclosure of which is herein incorporated by reference). T cell lines were able to be established from 5/6 normal donors using PSA peptide 141-150 and from 6/6 normal donors using PSA peptide 154-163. Moreover, PBMC were obtained from two prostate cancer patients. T cell lines were established from these PBMC cultures using peptide 154-163.

Some of these T cell lines have been phenotyped. As seen in Table 8, one cell line designated T-866 (T-Donor A), which was derived from pulsing with peptide 141-150, contains appreciable amounts of CD4+/CD8+ double positive cells and another cell line, designated T-1538 (T Donor B), derived from pulsing with peptide 154-163, shows a similar phenotype.

Four of the T cell lines derived from three different individuals were then assays for their ability to lyse human cells (Table 9). As seen in Table 9, the T cell line designated T-866, derived from peptide 141-150, was able to lyse T2 cells when pulsed with the appropriate peptide (141-150). No lysis was seen using the PSA negative human colon cancer cell line COLO-205. While 80% lysis was seen using the LNCAP PSA expressing human prostate cancer cell line. When employing the NK target K562, which measures non-specific lysis due to NK cell activity, only 23% lysis was obtained. Similar results were seen employing a different T cell line obtained from the same patient which was derived from pulsing with PSA peptide 154-163. Two additional T cell lines which were derived from peptide 154-163 were also analyzed. One was from a normal donor (T-1538) and one was from a prostate cancer patient (T-PC2; T Donor C). As can be seen in Table 9, employing both of these T cell lines, enhanced lysis was seen when the T2 cell line was pulsed with the 154-163 peptide and enhanced lysis was seen when employing the PSA expressing prostate specific cell line LNCAP, as compared to COLO-205 or K562. These studies demonstrate that T cell lines can be established using the peptides and protocols generated here which have the ability to lyse PSA expressing human prostate carcinoma cells.

TABLE 8

Flow cytometry analysis of PSA peptide specific T cells

| T-cell Line | PSA Peptide | CD3 | CD4 | CD8 | CD4/CD8 | CD56 |
|---|---|---|---|---|---|---|
| T-Donor A | 141-150 | 96 | 35 | 6.5 | 59 | 0 |
| T-Donor B | 154-163 | 94 | 5.2 | 32 | 62 | 0 |

Results are expressed in % positive cells.

TABLE 9

Cytotoxic effects of PSA peptide specific T cells

| | | % specific release (lysis) | | | | |
|---|---|---|---|---|---|---|
| T-cell Line | PSA Peptide | T2 | T2 + peptide | LNCAP | K562 | COLO-205 |
| T-Donor A | 141-150 | 10$^a$ | 40$^b$ | 80$^b$ | 23 | 7 |
| T-Donor A | 154-160 | 16 | 35$^b$ | 60$^b$ | 22 | 10 |
| T-Donor B | 154-160 | 10 | 40$^b$ | 29$^b$ | 3 | 10 |
| T-Donor C | 154-160 | 15 | 35$^b$ | 35$^b$ | 2 | 8 |

$^a$Percent of $^{111}$In specific release
24 hour cytotoxic assay (E:T ratio, 25:1)
$^b$p < 0.01 significant Example IV Construction and Characterization of Prostate Specific Antigen Oligo-Epitope Peptide Two 10-mer PSA peptides (PSA1 and PSA3) which were selected to conform to human HLA class 1-A2 motifs elicited PSA specific CTL responses in both normal donors and patients with prostate cancer. A longer PSA peptide (30-mer), designated prostate specific antigen oligo-epitope peptide (PSA-OP) comprising the shorter PSA-1 and PSA-3 peptide sequences, was investigated for the ability to mediate PSA specific cytotoxic T-cell activity (Table 10).

TABLE 10

Sequence of 30 amino acid PSA peptide

| PSA-OP (141-170) | FLTPKKLQCV/ | DLH/VISNDVCAQV/HPQKVTK | (Seq.ID No: 4) |
|---|---|---|---|
| PSA-1 (141-150) | FLTPKKLQCV | | (Seq.ID No: 1) |
| PSA-3 (154-163) | | VISNDVCAQV | (Seq.ID No: 2) |

Materials and Methods
Peptide Synthesis
PSA-OP was synthesized on an Applied Biosystems Model 432A peptide synthesizer. It operates on a 25 μmole scale and employs f-moc chemistry and feedback monitoring to control the coupling of each successive amino acid to the growing chain. The completed peptide is cleaved off the synthesis resin with trifluoroacetic acid and thioanisole/ethanedithiol as scavengers. Acid salts are extracted with tert-butyl methyl ether and the peptide is lyophilized from water to give approximately 64 mg powder. The powder is soluble at 2 mg/ml in 1% DMSO and sterile-filtered aliquots show a single sharp peak on C18 reverse phase high performance liquid chromatography.

Cell Cultures
Prostate carcinoma cell lines LNCAP and DU-145 [HLA-A2+] were purchased from American Type Culture Collection (Rockville, Md.). Cultures were mycoplasma free and were maintained in complete medium, Dulbecco's modified Eagle medium and RPMI1640 medium, respectively (Life Technologies Inc. GIBCO BRL, Grand Island, N.Y.) supplemented with 10% fetal bovine serum (FBS), 2 mM glutamine, 100 U/ml penicillin, and 100 μ/ml streptomycin (Life Technologies, Inc.). The 174CEM.T2 cell line (T2) (transport deletion mutant) is described in Anderson et al, 1993. CIR-A2 cell line is described in Storkus et al, 1987. T2 cell and CIRA2 cells were maintained in Iscove's modified Dulbecco's complete medium (IMDM) and RPMI1640 complete medium, respectively.

Generation of T Cell Lines
Peripheral blood mononuclear cells (PBMCs) were obtained from heparinized blood of healthy HLA-A2 donors using a lymphocyte separation medium gradient (Organon Technika, Durham, N.C.). The mononuclear cell fraction was washed 3 times and PBMCs were resuspended in complete medium: AIM V (Life Technologies, Inc.) supplemented with 5% human AB serum (Valley Biomedical, Winchester, Va.), 2 mM glutamine, 100 U/ml of penicillin, and 100 μg/ml of streptomycin (GIBCO). Cells ($2\times10^5$) in complete medium in a volume of 100 μl were put into each well of a 96-well flat-bottom assay plate (Corning, Costar Corp., Cambridge, Mass.). Peptides were added to cultures at a final concentration of 50 μl/ml. Cultures were incubated for 5 days at 37° C. in a humidified atmosphere containing 5% $CO_2$. After removal of the peptide-containing medium, the cultures were then provided with human IL-2-(Cetus) (20 U/ml) for 11 days, with IL-2-containing medium being replenished every 3 days. The incubation time of 5 days with peptide plus 11 days with IL-2 constitutes one cycle. Primary cultures were restimulated with the same peptide (50 μg/ml) on day 1 of each cycle. Irradiated (4,000 rads) autologous PBMCs ($1\times10^6$) were added in a volume of 100 μl in complete medium (AIM-V) and used as antigen presenting cells.

Cytotoxic Assays
Various target cells were labeled with 50 μCi of $^{111}$In-oxyquinoline (Medi-Physics Inc., Arlington, Ill.) for 15 minutes at room temperature. Target cells ($0.2\times10^4$) in 100 μl of complete medium (see below) were added to each of 96 wells in flat bottom assay plates (Corning Costar Corp.). The labeled targets were incubated with peptides at a final concentration of 50 μg/ml for 60 min at 37° C. in 5% $CO_2$ before adding effector cells. Effector cells were suspended in 100 μl of complete medium supplemented with 5% pooled human AB serum and added to target cells. The plates were incubated at 37° C. for 16 hours. Supernatants were harvested for γ-counting using harvester frames (Skatron, Inc. Sterling, Va.). Determinations were carried out in triplicate and standard deviations were calculated. All experiments were carried out three times. Specific Lysis was calculated using the following formula:

$$\% \text{ of Specific Release} = \frac{\text{observed release}(cpm) - \text{spontaneous release}(cpm)}{\text{total releae}(cpm) - \text{spontaneous release}(cpm)} \times 100$$

Spontaneous release was determined from wells to which 100 μl of complete medium, instead of effector cells was added. Total releasable radioactivity was obtained after treatment of target cells with 2.5% Triton X-100.

Experiments using protease inhibitors were performed using C1R-A2 cells as target cells pulsed with 10 μg/ml of PSA-OP for 3 hr. Peptide pulsed target cells were incubated with protease inhibitors. Protease inhibitors used were E64, carboxypeptidase inhibitor, plummer inhibitor, and captopril (angiotension converting enzyme inhibitor) at various concentrations ($10^{-5}$, $10^{-6}$, $10^{-7}$ M). CTL activity was determined by the CTL assay described above.

Limiting Dilution Analysis
Limiting dilution assays were used for the determination of precursor frequencies to PSA-1, PSA-3 and PSA-OP. Various number of PBMCs were seeded in 96-well flat bottom plates (Corning Costar) with $1\times10^4$ autologous PBMC irradiated with 4,000 rads and incubated with 50 μg/ml of PSA peptide. Cells were cultured in complete medium as described previously. At least 48 cultures were set up for each dilution. Cultures were incubated for 5 days at 37° C. in a humidified atmosphere containing 5% $CO_2$ and then provided with fresh medium containing human IL-2 for 11 days, with IL-2-containing medium being replenished every 72 hr as shown below for CTLs generation. After two cycles of stimulation specific cytotoxic activity was tested for each single well, against CIR-A2 target cells with or without incubation with peptide. Cytotoxic assays were similar to the method described above. The unlabelled K562 cells were added to the microwells containing responder cells. After 1 hr incubation at 37° C. target cells were added into each well and incubated for 6 hrs at 37° C. Precursor frequencies were calculated by $X^2$ minimization.

Flow Cytometry
Single-color flow cytometric analysis: $1\times10^6$ cells were washed three times with cold $Ca^{2+}$- and $Mg^{2+}$-free Dulbecco's phosphate-buffered saline (DPBS) and then stained for 1 hr with 1 μg of monoclonal antibody (MAb) against CD3, CD4, CD8, CD56, CD19, HLA class II (HLA-DR) (Becton Dickinson, San Jose, Calif.). HLA class I (W6/32) (Seratec, Sussex, England), and MOPC-21 (Cappel/Organon Teknika Corp., West Chester, Pa.) in a volume of 100 μl of PBS containing 1% bovine serum albumin. The cells were then washed three times with cold DPBS and incubated for an additional hour in the presence of 1:100 dilution (volume of 100 μl PBS containing 1% bovine serum albumin) of fluorescein-conjugated goat anti-mouse immunoglobulin (Ig) (Kirkeggard and Perry Labs, Gaitheresburg, Md.). The cells were again washed three times with DPBS and resuspended in DPBS at the concentration of $1\times10^6$ cells/ml. The cells were immediately analyzed using a Becton Dickinson FAC-Scan equipped with a blue laser with an excitation of 15 nW at 488 nm. Data were gathered from 10,000 live cells and used to generate results.

Dual color flow cytometric analysis: The procedure for two-color flow cytometry analysis was similar to that used for single-color analysis with the following exceptions. The MAbs used were anti-CD4 fluorescein conjugate, anti-CD8 phycoerythrin conjugate, anti IgG1 fluorescein conjugate and anti-1gG2a phycoerythrin conjugate (Becton Dickinson). Staining was done simultaneously for 1 hr after which cells were washed three times, resuspended as above, and immediately analyzed using a Becton Dickinson FACSort equipped with a blue laser with an excitation of 15 nW at 488 nm and the Lysis II program.

Peptide Binding to HLA-A2

Binding of PSA-1 and PSA-3 and PSA-OP peptides to the HLA-A2 molecules was evaluated by upregulation of the expression of these molecules on the cell surface of T2 cells as demonstrated by flow cytometry. $1\times10^6$ cells in serum-free IMDM were incubated with peptides at the concentration of 50 μg/ml in 24-well culture plates at 37° C. in 5% $CO_2$. Flow cytometry for peptide binding was performed using T2 cells and single color analysis. After cells were washed three times in DPBS as above, they were incubated for 1 hr with HLA-A2 specific MAb A2,69 (One lambda, Inc., Canoga Park, Calif.), using 10 μl of a 1×working dilution per $10^6$ cells. MOPC-21 (Cappel/Organon Teknika Corp.) was used as isotype control. The cells were then washed three times and incubated with 1:100 dilution of fluorescein (FITC) labeled anti-mouse IgG (Kirkegaard & Perry, Gaithersburg, Md.). Analysis was carried out using the FACScan as described above. Cells were maintained on ice during all cell preparation and staining unless otherwise stated.

HLA Typing

The HLA phenotyping of donor A (HLA-A2,24; B27,35; C2,4; DR B1*0101,B1*1104; DQw B10501,B1*0301; DRw B3*0202) and donor B(HLA-A2, 29; B7,44; Cw5-; DR13,-; DQw6,-; DRw52,-) was performed by the Blood Bank of NIH on PBMC using a standard antibody-dependent micro-cytotoxicity assay and a defined panel of anti-HLA antisera or DNA assay. The following HLA phenotypes were found for healthy donors utilized for PSA (rV-PSA) was generated by the methods described in Hodge et al, 1995. The PSA gene was isolated as a complementary DNA (cDNA) clone from a human prostate carcinoma cell cDNA library. The PSA cDNA was inserted under the control of the vaccinia 40K promoter into the Hind III M region of the genome of the attenuated Wyeth strain vaccine virus.

A recombinant vaccinia virus expressing PSA-OP was made by the same methodology (Hodge et al, 1995).

Vaccinia Virus Infection of Prostate Carcinoma Cells

DU-145 target cells at the concentration of $1\times10^7$ per ml in complete RPMI-1640 medium supplemented with 0.1% bovine serum albumin were incubated with an equal volume of vaccinia virus (10 MOI) in the same medium at 37° C. for 1.5 hours. The cells were then seeded at $10^5$ cell per ml in complete medium with 10% FBS, into a 24-well culture plates at 37° C. in 5% $CO_2$ for 24 hr before being utilized as targets in cytotoxic assay experiments, bPSA production from rV-PSA vaccinia virus was evaluated by immunoradioassay kit purchased from Tandem Co.

Statistical Analysis

Statistical analysis of differences between means was done by a two tailed paired t-test.

Results

Two T-cell lines from different normal donors were established by in vitro stimulation with PSA-OP. The T-cell lines were phenotypically CD4+, CD8+, or CD4+/CD8+ and CD56− as shown in Table 11.

TABLE 11

| Flow Cytometric Analysis Of Surface Markers On T Cell Lines | | | | | |
|---|---|---|---|---|---|
| T Cell Line | CD3+ | CD4+/CD8− | CD4−/CD8+ | CD4+/CD8+ | CD56+ |
| T/PSA-OP-1 | 93.80(94.10) | 5.83(109.00) | 32.00(4550.00) | 62.00(139/110) | neg |
| T/PSA-OP-2 | 95.86(167.77) | 52.38(2505.00) | 41.55(2151.00) | 4.46(153/3325) | neg |

Results are expressed as percentage of fluorescent cells and (x/y) mean fluorescent intensity per cell. Marker expression was considered negative (neg)when lower that 4%. Results are expressed as a percentage of each T-cell line reactive with mAbs. Routinely, 2.0-4.0% of cells are stained when treated either with no priming MAbs or an isotype related control MAb.

The human CTLs lysed PSA-OP as well as PSA-1 or PSA-3 pulsed CIR-A2 cells as shown in Table 12.

TABLE 12

| CTL activity of PSA-OP specific T cell lines | | | | | |
|---|---|---|---|---|---|
| Donor | No peptide | PSA-OP | PSA-1 | PSA-2 | PSA-3 |
| T/PSA-OP-1 | 7.9(2.7) | 32.3*(0.87) | 8.4(4.0) | 1.8(0.30) | 28.7*(1.12) |
| T/PSA-OP-2 | 0.0(0.06) | 16.5*(1.0) | 14.3*(0.6) | 6.4(1.40) | 16.5*(1.0) |

T/PSA-OP-2 specifically lysed CIR-A2 cells pulsed with PSA-OP, PSA-1 and PSA-3 peptides, while T/PSA-OP-1 cell line only lysed CIRA2 when pulsed with PSA-OP and PSA-3. CIRA2 cells have been pulsed with 50 μg/ml of PSA peptide for 3 h, before to be labeled with $^{111}$In and utilized as target in 18 h CTL cytotoxic assay. Results are expressed as % of Specific release (SD) at the E:T ratio of 25:1.
*P < 0.02

The human CTLs also lysed PSA+ HLA-A2+ human prostate cancer cells as shown in Table 13.

TABLE 13

| CTL activity of PSA-OP specific T cell lines against HLA-A2001+, PSA-producing human Prostate Carcinoma Cells | | | |
|---|---|---|---|
| | LNCAP | | |
| Donor | 12.5:1 | 25:1 | E:T ratio |
| T/PSA-OP-1 | 32.54*(6.6) | 50.4*(6.4) | |
| T/PSA-OP-2 | 14.60*(3.7) | 24.8*(1.6) | |

Established CTLs from Donors 1 & 2 lyse LNCAP Prostate carcinoma cells.
$10^6$ LNCAP cells have been labelled with $^{111}$In and used as targets in 18 h CTL cytotoxic assay.
Results are here expressed as % of Specific Release (SD). P < 0.016.

The HLA-A2+ DU-145 prostatic carcinoma cell line was infected with vaccinia virus engineered with the PSA gene or the PSA-OP gene. The DU-145 cells infected with the rV-PSA vaccinia virus expressed PSA as shown in Table 14.

TABLE 14

PSA production by DU-145 infected with wt and rV-PSA vaccinia virus

| Prostatic Carcinoma Cells | 4 hours [pg/ml] | 24 hours [pg/ml] |
|---|---|---|
| DU-145 (WT) | 1.2 (0.15) | 1.7 (1.20) |
| DU-145 (rV-PSA) | 5.1 (0.50) | 12.0 (4.50) |
| LNCAP | ND | 232.0 (4.60) |

DU-145 cells production of PSA after rV-PSA vaccinia virus infection.
DU-145 have been incubated with wild type of rV-PSA Vaccinia virus (10 MOI) for 4 and 24 h before the supernatant was harvested and evaluated for PSA production by IRMA detection PSA kit (tandem).
LNCAP prostate cancer carcinoma cells have been used as a positive control since they are known to produce large amounts of PSA in 24 h.
Results are expressed as pg/ml (SD) per $10^6$ of cells.

The ability of the human PSA-OP specific T lymphocyte cell lines to lyse the rV-PSA or rV-PSA-OP vaccinia virus infected DU-145 prostatic cells was determined. As Table 15 shows, the human T-cell lines lysed rV-PSA infected targets as well as rV-PSA-OP infected targets.

TABLE 15

CTL activity of PSA-OP specific T cell lines against HLA-A2001 + DU -145 prostate cell line, infected with vaccinia virus, engineered with PSA gene and PSA-OP mini-gene

| T Cell Line | DU-145 [WT] | | DU-145 [rV-PSA] | | DU-145 [rV-PSA-OP] | | E:T ratio |
|---|---|---|---|---|---|---|---|
| | 12.5:1 | 25.1 | 12.5:1 | 25:1 | 12.5:1 | 25:1 | |
| T/PSA-OP-1 | 15.0(3.8) | 26.5(6.1) | 31.8*(5.0) | 45.7*(6.1) | 32.5*(6.6) | 50.4*(6.4) | |
| T/PSA-OP-2 | 0.0(2.0) | 6.2(4.9) | 4.0*(2.1) | 10.5*(2.8) | 10.9*(1.4) | 14.6*(3.7) | |

Established CTLs lysed DU-145 prostate cancer cells after infection with rV-PSA and rV-PSA-OP vaccinia virus. DU-145 cells have been incubated with Vaccinia virus (10 MOI) wild type or carrying the PSA gene or PSA-OP mini-gene for 24 h before being labeled and incubated with effector cells. The ability of rV-PSA infected cells to produce PSA was evaluated by a radio immunoassay kit from Tandem. Results are here expressed as % of Specific Release (SD).
*P < 0.05.

The ability of PSA-OP to directly bind to a HLA Class I-A2 molecule was determined. The results in Table 16 showed that PSA-OP did not bind HLA-A2 as indicated by the lack of upregulation of A2 expression on 174 CEM-T2 cells.

TABLE 16

Binding of PSA peptides to the HLA class-I A2001 molecule

| Peptide | #T2 binding | *Predicted binding |
|---|---|---|
| None | 16.88 | Neg |
| PSA [42-51] | 51.44 | Neg |
| PSA-OP | 63.28 | Neg |
| PSA-1 | 127.73 | Pos |
| PSA-3 | 123.71 | Pos |
| MTX [58-66] | 157.86 | Pos |

PSA-OP does not bind the HLA class-I A2001 molecules on T2 cell surface
*Predicted binding on the basis of published motifs: Pos = positive Neg = negative
Reaction of T2 cells with anti-HLA-A2 mAb after the cells had been incubated for 24 h with control peptides and PSA peptides (50 µg/ml/$10^6$ cells), PSA [42-51] was considered as a negative control peptide, since it is unable to bind HLA class I-A2, while PSA-1, PSA-3, MTX [58-66] were considered as a positive control. The results are expressed as relative fluorescence (mean intensity) and 100 was arbitrarily chosen as a cut off value for positivity.

Since it was shown that the 30-mer PSA-OP peptide did not directly bind to HLA class I-A2 molecules but did stimulate cytotoxic cells to lyse PSA$^+$ HLA class I-A2 targets, studies were undertaken to determine if the 30-mer PSA-OP peptide was cleaved to smaller peptides by proteolytic activity to allow it to interact with HLA class I-A2 molecules.

The effects of protease inhibitors on CTL mediated killing of CIR-A2 cells pulsed with PSA-OP peptide was determined. The results shown in Table 17 show decreased cytotoxicity in the presence of protease inhibitors. These results indicate that the PSA-OP is cleaved by proteases on the cell surface of the target cells into shorter peptides which, in turn, interact with HLA-A2 molecules and as a consequence induce specific CTL lysis of CIR-A2 target cells.

TABLE 17

Effects of protease inhibitors on CTL mediated killing of CIRA2 Cells Pulsed with PSA-OP Peptide

| Peptides Pulsed | Donor-1 PSA-OP | | | |
|---|---|---|---|---|
| in Human Serum | No peptide | | PSA-OP peptide [50 µg/ml] | |
| Medium | 7.7 | (1.9) | 26.1* | (4.3) |
| E 64 [$10^{-6}$ M] | 11.9 | (1.7) | 13.7 | (0.6) |
| Plummer's [$10^{-5}$ M] | 10.7 | (2.0) | 18.7* | (2.4) |

TABLE 17-continued

Effects of protease inhibitors on CTL mediated killing of CIRA2 Cells Pulsed with PSA-OP Peptide

| Peptides Pulsed | Donor-1 PSA-OP | | | |
|---|---|---|---|---|
| in Human Serum | No peptide | | PSA-OP peptide [50 µg/ml] | |
| Captopril [$10^{-6}$ M] | 15.8 | (2.1) | 11.0 | (2.6) |
| PCI [$10^{-5}$ M] | 13.2 | (1.6) | 13.7 | (3.2) |

Extracellular carboxypeptidase inhibitors (E64, captopril and PCI) block the lysis of CIR-A2 cells pulsed with PSA-OP peptide by established CTLs.
Results are expressed as % of Specific Release (+/−SD) at 25:1 E:T ratio.
*P < 0.03.

Precursor frequency (PF) studies showed that PF for PSA-1, alone, and PSA-3, alone, varied from donor to donor. In contrast, the PF for PSA-OP was strikingly similar from donor to donor as shown in Table 18.

TABLE 18

Precursor Frequency Study

| | % of negative microcolonies | | | | Number of |
|---|---|---|---|---|---|
| Donor | 10,000 | 5,000 | 1,000 | 500 | precursors |
| T/PSA-OP 2 donor | | | | | |
| PSA-OP | 91.6 | 89.3 | 100.0 | 100.0 | 1/80006 |
| PSA-1 | 47.9 | 75.0 | 93.7 | 95.8 | 1/14695 |
| PSA-3 | 95.8 | 97.8 | 100.0 | 100.0 | 1/244200 |

TABLE 18-continued

Precursor Frequency Study

| Donor | % of negative microcolonies | | | | Number of precursors |
|---|---|---|---|---|---|
| | 10,000 | 5,000 | 1,000 | 500 | |
| T/PSA-OP 3 donor | | | | | |
| PSA-OP | 93.7 | 95.8 | 95.8 | 96.9 | 1/70229 |
| PSA-1 | 93.7 | 97.9 | 100.0 | 100.0 | 1/181480 |
| PSA-3 | 89.6 | 93.7 | 95.8 | 97.6 | 1/59279 |

CTL precursors specific for PSA-OP, PSA-1 and PSA-3 peptides are present in PBLs isolated from male HLA-A2001+ donors after two cycles of stimulation with PSA peptides. Precursors' cytotoxic effects were evaluated against CIRA2 pulsed for 3 h with respective PSA peptides in the presence of cold K562 (10,000/well).

Thus, PSA-OP as an immunogen offers distinct advantages over the use of PSA-1 alone or PSA-3 alone in eliciting consistent numbers of cytotoxic T lymphocytes from individual to individual. Furthermore, PSA-OP comprises more than one epitope peptide sequence which may fit the consensus motif for a variety of HLA-class I molecule types including HLA-A2, A3, A11, Aw68 and B53. HLA-A2 is present in approximately 50% of North American Caucasians and 34% of African Americans. HLA-A3 is present in 26 and 17% of North American caucasians and African Americans, respectively. HLA-A11 is present in 40% of the Asian population and HLA-B53 is present in 22% of African Americans. Consequently, PSA-OP may be useful as an immunogen in eliciting PSA specific immune responses in a broad segment of the human population.

This invention has been described in detail including the preferred embodiments thereof. However, it will be appreciated that those skilled in the art, upon consideration of this disclosure, may make modifications and improvements thereon without departing from the spirit and scope of the invention as set forth in the claims.

References and patents referred to are incorporated herein by reference.

REFERENCES

Anderson, K. S., Alexander, J., Wei, M. and Cresswell, P. Intercellular transport of class I MHC molecules in antigen processing mutant cell lines. *J. Immunology* 151:3407-3419, 1993.

Armbruster, D. A. Prostate-specific antigen: biochemistry, analytical methods, and clinical application. *Clinical Chemistry*, 39:181-195, (1993).

Bilhartz, D. L., Tindall, D. J., and Oesterling, J. E. Prostate-specific antigen and prostatic acid phosphatase: biomolecular and physiological characteristics. *Urology*, 38:95-102, (1991).

Brawer, M. K., and Lange, P. H. Prostate-specific antigen and premalignant change: implications for early detection. *CA Cancer Journal Clinic*, 39:361-375, (1989).

Carter, H. B., and Coffey, D. S. The prostate: an increasing medical problem. *Prostate*, 16:39-48, (1990).

Chatterjee, M. B., Foon, K. A., and Kohler, H. Idiotypic antibody immunotherapy of cancer. *Cancer Immunology and Immunotherapy*, 38:75-82, (1994).

Cheever, M. A., Chen, W., Disis, M. T., and Peace, D. J. T-cell immunity to oncogenic proteins including mutated RAS and chimeric BCR-ABL. *Annals of the New York Academy of Science*, 690:101-112, (1993).

Choe, B. K., Frost, P., Morrison, M. K., and Rose, N R. Natural killer cell activity of prostatic cancer patients. *Cancer Investigations*, 5:285-291, (1987).

Conry, R. M., Salch, M. N., Schlom, J., and LoBuglio, A. F. Breaking tolerance to carcinoembryonic antigen with a recombinant vaccinia virus vaccine in man. *American Association of Cancer Research* (Abstract), (1994).

Correale, P., Zaremba, S., Nieroda, C., Zhu, M. Z., Schmitz, J., Schlom, J., and Tsang, K. Y. In vitro stimulation of human cytotoxic T lymphocytes specific for peptides derived from prostate specific antigen. *9th International Congress of Immunology* July 23-29, (Abstract #3449), (1995).

Disis, M. L., Smith, J. W., Murphy, A. A., Chen, W., and Cheever, M. A. In vitro generation of human cytolytic T-cells specific for peptides from the HER-2/-neu protooncogene protein. *Cancer Research*, 54:1071-1076, (1994).

Donovan, J. F., Lubaroff, D. M., and Williams, R. D. Immunotherapy of prostate cancer. *Problems In Urology*, 4:489-505, (1990).

Foon, K. A., Chakraborty, M., John, W., Sherratt, A., Kohler, H., and Bhattacharya-Chatterjee, M. Active immunity to the carcinoembryonic antigen (CEA) in patients treated with an anti-idiotype monoclonal antibody vaccine. *Society for Biological Therapy* (Abstract), (1994).

Gauthier, E. R., Chapdelaine, P., Tremblay, R. R., and Dube, J. Y. Characterization of rhesus monkey prostate specific antigen cDNA. *Biochemica Biophysica Acta*, 1174:207-210, (1993).

Gritz, L., Destree, A., Cormier, N., Day, E., Stallard, V., Caiazzo, T., Mazzara, G., and Panicali, D. Generation of hybrid genes and proteins by vaccinia virus-mediated recombination: application to human immunodeficiency virus type 1 env. *J. Virol.* 64:5948-5957, (1990).

Helling, F., and Livingston, P. O. Ganglioside conjugate vaccines. Immunotherapy against tumors of neuroectodermal origin. *Molecular and Chemical Neuropathology*, 21:299-309, (1994).

Helling, F., Calves, M., Shang, Y., Oettgen, H. F., and Livingston, P. O. Construction of immunogenic GD3-conjugate vaccines. *Annals of the New York Academy of Science*, 690:396-397, (1993).

Hodge, J. W., Scholm, J., Donohue, S. J., Tomaszewski, J. E., Wheeler, C. W., Levine, B. S, Gritz, L., Panicali, D., Kantor, J. A., A Recombinant Vaccinia Virus Expressing Human Prostate-Specific Antigen (PSA): Safety and Immunogenicity in a Non-Human Primate. *Int. J. Cancer* Vol. 63(2):231-7 (1995).

Huang, C, L., Brassil, D., Rozzell, M., Schellhammer, P. F., and Wright, G. L. Comparison of prostate secretory protein with prostate specific antigen and prostatic acid phosphatase as a serum biomarker for diagnosis and monitoring patients with prostate carcinoma. *Prostate*, 23: 201-212, (1993).

Ioannides, C. G., Fisk, B., Fan, D., Biddison, W. E., Wharton, J. T., and O'Brian, C. Cytotoxic T cells isolated from ovarian malignant ascites recognize a peptide derived from the HER-2/neu proto-oncogene. *Cellular Immunology*, 151:225-234, (1993).

Irvine, K., Kantor, J., and Schlom, J. Comparison of a CEA-recombinant vaccinia virus, purified CEA, and an anti-idiotype antibody bearing the image of a CEA epitope in the treatment and prevention of CEA-expressing tumors. *Vaccine Research*, 2:79-94, (1993).

Isaacs, J. T., Feitz, W. F., and Scheres, J. Establishment and characterization of seven Dunning rat prostatic cancer cell lines and their use in developing methods for predicting metastatic abilities of prostatic cancers. *Prostate*, 9:261-281, (1986).

Jenkins, S., Gritz, L., Fedor, C., O'Neil, E., Cohen, L. and Panicali, D. Formation of lentivirus particles in mammalian cells infected with recombinant fowlpox virus. *AIDS Research and Human Retroviruses* 7:991-998, (1991).

Kantor, J., Irvine, K., Abrams, S., Kaufman, H., Dipietro, J., and Schlom, J. Antitumor activity and immune responses induced by a recombinant carcinoembryonic antigen-vaccinia virus vaccine. *Journal of the National Cancer Institute,* 84:1084-1091, (1992a).

Kantor, J., Irvine, K., Abrams, S., Snoy, P., Olsen, R., Greiner, J., Kaufman, H., Eggensperger, D., and Shlom, J. Immunogenicity and safety of a recombinant vaccinia virus vaccine expressing the carcinoembryonic antigen gene in a nonhuman primate. *Cancer Research,* 52:6917-6925, (1992b).

Karr, J. F., Kantor, J. A., Hand, P. H., Eggensperger, D. L., and Schlom, J. The presence of prostate-specific antigen-related gene in primates and the expression of recombinant human prostate-specific antigen in a transfected murine cell line. *Cancer Research Vol.* 55 (11):2455-62, (1995).

Kaufman, H., Schlom, J., and Kantor, J. A recombinant vaccinia virus expressing human carcinoembryonic antigen (CEA). *International Journal of Cancer,* 48:900-907, (1991).

Kleer, E., and Oesterling, J. E. PSA and staging of localized prostate cancer. *Urologic Clinics of North America,* 20:695-704, (1993).

Lilja, H. Structure, function, and regulation of the enzyme activity of prostate-specific antigen. *World Journal of Urology,* 11:188-191, (1993).

Livingston, P. O., Calves, M. J., Helling, F., Zollinger, W. D., Blake, M. S., and Lowell, G. H. GD3/proteosome vaccines induce consistent IgM antibodies against the ganglioside GD3. *Vaccine,* 12:1199-1204, (1993).

Lundwall, A., and Lilja, H. Molecular cloning of human prostate specific antigen cDNA. *FEBS Letters,* 214:317-322, (1987).

McEntee, M., Isaacs, W., and Smith, C. Adenocarcinoma of the canine prostate: immunohistochemical examination for secretory antigens. *Prostate,* 11:163-170, (1987).

Moss, B. Generation of recombinant vaccinia viruses. Current Protocols in *Molecular Biology,* 2:16.15.1-16.18.9, (1993).

Oesterling, J. E. Prostate specific antigen: a critical assessment of the most useful tumor marker for adenocarcinoma of the prostate. *Journal of Urology,* 145:907-9-23, (1991).

Panicali, D., Grzelecki, A. and Huang, C. Vaccinia virus vectors utilizing the β-galactosidase assay for rapid selection of recombinant viruses and measurement of gene expression. *Gene* 47:193-199, (1986).

Paoletti, E., Tartaglia, J., and Cox, W. I. Immunotherapeutic strategies for cancer using poxvirus vectors. *Annals of the New York Academy of Sciences,* 690:292-300, (1993).

Peace, D. J., Xue, B., Sosman, J. A., and Zhang, Y. In vitro immunization of human cytotoxic T lymphocytes specific for peptides derived from prostate specific antigen. *Cancer Vaccines: Structural Basis for Vaccine Development* (Abstract), (1994).

Powrie, F., and Coffman, R. L. Cytokine regulation of T-cell function: potential for therapeutic intervention. *Immunology Today,* 14:270-274, (1993).

Ravindranath, M. H., Brazeau, S. M., and Morton, D. L. Efficacy of tumor cell vaccine after incorporating monophosphoryl A (MPL) in tumor cell membranes containing tumor associated ganglioside. *Experimentia,* 50:648-653, (1994).

Ritter, G., Boosfeld, E., Adiuri, R., Calves, M., Oettgen, H. F., Old, L. J., and Livingston, P. Antibody response to immunization with ganglioside GD3 and GD3 congeners (lactones, amide, and ganglisidol) in patients with malignant melanoma. *International Journal of Cancer,* 48:379-385, (1991).

Schellhammer, P. F., and Wright, G. L. Biomolecular and clinical characteristics of PSA and other candidate prostate tumor markers. *Urologic Clinics of North America,* 20:597-606, (1993).

Schlom, J., Kantor, J., Abrams, S., Tsang, K. Y., Panicali, D., and Hamilton, J. M. Strategies for the development of recombinant vaccines for the immunotherapy of breast cancer. *Breast Cancer Research and Treatment,* In Press.

Schroder, F. H. Experimental Models in the study of prostate cancer. Prostate Cancer. In: *International Perspectives in Urology.,* 3:343-377, (1982).

Storkus, W. J. Howell, D. N., Salter, R. D., Dawson, J. R., and Cresswell, P. N K susceptibility varies inversely with target cell class I HLA antigen expression. *J. Immunology* 138:1657-1659, 1987.

Tsang, K. Y., Nieroda, C. A., De Filippi, R., Chung, Y. K., Yamaue, H., Greiner, J. W., and Schlom, J. Induction of human cytotoxic T cell lines directed against point-mutated p21 Ras-derived synthetic peptides. *Vaccine Research,* 3:183-193, (1994).

Wakui, S., Furusato, M., Nomura, Y., Asari, M., and Kano, Y. Lectin histo-chemical study of the prostate gland of the rhesus monkey (Macaca mulatta). *Journal of Anatomy,* 181:127-131, (1992).

Wang, M. C., Kuriyama, M., Papsidero, L. D., Loor, R. M., Valenzuela, L. A., Murphy, G. P., and Chu, T. M. Prostate antigen of human cancer patients. *Methods in Cancer Research,* 19:179-197, (1982).

Wang, M. C., Vaienzuela, L. A., Murphy, G. P., and Chu, T. M. Purification of a human prostate specific antigen. *Investigations in Urology,* 17:159-163, (1979).

Zietman, A. L., Shipley, W. L., and Willett, C. G. Residual disease after radical surgery or radiation therapy for prostate cancer. Clinical significance and therapeutic implications. *Cancer,* 71:959-969, (1993).

What is claimed is:

1. A method for eliciting an immune response against prostate specific antigen (PSA) for treating a human comprising:
   (a) administering to the human a priming inoculation of an effective amount of a first recombinant virus, wherein the first recombinant virus comprises a DNA sequence encoding PSA or a cytotoxic T-cell- (CTL-) eliciting epitope thereof; and
   (b) administering to the human one or more boosting inoculations of an effective amount of a second recombinant virus of a different genus, wherein the second recombinant virus comprises a DNA sequence encoding PSA or a CTL-eliciting epitope thereof.

2. The method of claim 1, wherein the first recombinant virus is an orthopox virus and the second recombinant virus is an avipox virus.

3. The method of claim 2, wherein the orthopox virus is vaccinia virus and the avipox virus is fowlpox virus.

4. The method of claim 1, wherein the first and second recombinant viruses further comprise a DNA sequence encoding an immunoenhancing molecule selected from the group consisting of influenza peptide, tetanus toxoid, tetanus toxoid CD4-epitope, *Pseudomonas* exotoxin A and poly-L-lysine.

5. The method of claim 1, wherein the first and second recombinant viruses are administered at a dose of about 0.5 mg to about 100 mg per kilogram of the human.

6. The method of claim 1, wherein the first and second recombinant viruses are administered at a dose of $10^5$ plaque-forming units (pfu) to $10^9$ pfu.

7. The method of claim 6, wherein the first and second recombinant viruses are administered at a dose of $10^7$ pfu.

8. The method of claim 1, wherein the second recombinant virus is administered at one or more periodic intervals after the first recombinant virus.

9. The method of claim 8, wherein the second recombinant virus is administered in one or more doses after the first recombinant virus at a periodic interval of 1-3 months.

10. A method for stimulating the immune system of a human to produce an immune response against prostate specific antigen (PSA) to prevent the establishment and growth of PSA-positive carcinoma cells comprising:
    (a) administering to the human a priming inoculation of an effective amount of a first recombinant virus, wherein the first recombinant virus comprises a DNA sequence encoding PSA or a cytotoxic T-cell- (CTL-) epitope thereof; and
    (b) administering to the human one or more boosting inoculations of an effective amount of a second recombinant virus of a different genus, wherein the second recombinant virus comprises a DNA sequence encoding PSA or a CTL-eliciting epitope thereof;
    wherein the first and second recombinant viruses cause the expression of the PSA or a CTL-eliciting epitope thereof in the human in an amount sufficient to effect the stimulation.

11. The method of claim 10, wherein the first recombinant virus is an orthopox virus and the second recombinant virus is an avipox virus.

12. The method of claim 11, wherein the orthopox virus is vaccinia virus and the avipox virus is fowlpox virus.

13. The method of claim 10, wherein the first and second recombinant viruses further comprise a DNA sequence encoding an immunoenhancing molecule selected from the group consisting of influenza peptide, tetanus toxoid, tetanus toxoid CD4-epitope, *Pseudomonas* exotoxin A and poly-L-lysine.

14. The method of claim 10, wherein the first and second recombinant viruses are administered at a dose of about 0.5 mg to about 100 mg per kilogram of the human.

15. The method of claim 10, wherein the first and second recombinant viruses are administered at a dose of $10^5$ plaque-forming units (pfu) to $10^9$ pfu.

16. The method of claim 15, wherein the first and second recombinant viruses are administered at a dose of $10^7$ pfu.

17. The method of claim 10, wherein the second recombinant virus is administered at one or more periodic intervals after the first recombinant virus.

18. The method of claim 17, wherein the second recombinant virus is administered in one or more doses after the first recombinant virus at a periodic interval of 1-3 months.

* * * * *

SEQUENCE LISTING

```
<160> NUMBER OF SEQ ID NOS: 17

<210> SEQ ID NO 1
<211> LENGTH: 10
<212> TYPE: PRT
<213> ORGANISM: Artificial Sequence
<220> FEATURE:
<223> OTHER INFORMATION: Synthetic Polypeptide
```

```
<400> SEQUENCE: 1

Phe Leu Thr Pro Lys Lys Leu Gln Cys Val
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 2

Val Ile Ser Asn Asp Val Cys Ala Gln Val
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 3

Gln Val His Pro Gln Lys Val Thr Lys
1               5

<210> SEQ ID NO 4
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 4

Phe Leu Thr Pro Lys Lys Leu Gln Cys Val Asp Leu His Val Ile Ser
1               5                   10                  15

Asn Asp Val Cys Ala Gln Val His Pro Gln Lys Val Thr Lys
            20                  25                  30

<210> SEQ ID NO 5
<211> LENGTH: 90
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: CDS
<222> LOCATION: (1)..(90)

<400> SEQUENCE: 5 ttc ttg acc cca aag aaa ctt cag tgt gtg gac ctc cat gtt att tcc      48
Phe Leu Thr Pro Lys Lys Leu Gln Cys Val Asp Leu His Val Ile Ser
1               5                   10                  15 aat gac gtg tct gcg caa gtt cac cct cag aag gtg acc aag             90
Asn Asp Val Ser Ala Gln Val His Pro Gln Lys Val Thr Lys
            20                  25                  30

<210> SEQ ID NO 6
<211> LENGTH: 90
<212> TYPE: DNA
<213> ORGANISM: Artificial Sequence
<220> FEATURE:
<223> OTHER INFORMATION: Synthetic Polynucleotide

<400> SEQUENCE: 6
cttggtcacc ttctgagggt gaacttgcgc acacacgtca ttggaaataa catggaggtc      60
```
cacacactga agtttctttg gggtcaagaa                                          90

<210> SEQ ID NO 7
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 7

Phe Leu Arg Pro Arg Ser Leu Gln Cys Val
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 8

Phe Ser Phe Pro Asp Asp Leu Gln Cys Val
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 9

Lys Leu Gln Cys Val Asp Leu His Val
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 10

Ser Leu Gln Cys Val Ser Leu His Leu
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 11

Asp Leu Gln Cys Val Asp Leu Lys Ile
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 12

Leu Leu Ser Asn Asp Met Cys Ala Arg Ala
1               5                   10

```
<210> SEQ ID NO 13
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 13

Ile Leu Pro Asn Asp Glu Cys Glu Lys Ala
1               5                   10

<210> SEQ ID NO 14
<211> LENGTH: 246
<212> TYPE: DNA
<213> ORGANISM: Artificial Sequence
<220> FEATURE:
<223> OTHER INFORMATION: Synthetic Polynucleotide

<400> SEQUENCE: 14
gtaccaccat gaggtacatg attttaggct tgctcgccct tgcggcagtc tgcagcgctg        60
atatgtttaa taattttacc gttagctttt ggttgagggt tcctaaagta tctgctagtc       120
atttagaaca agagttcttg accccaaaga aacttcagtg tgtggacctc catgttattt       180
ccaatgacgt gtgtgcgcaa gttcaccctc agaaggtgac caagttcatg ctgtgttagt       240
ttttgt                                                                  246

<210> SEQ ID NO 15
<211> LENGTH: 246
<212> TYPE: DNA
<213> ORGANISM: Artificial Sequence
<220> FEATURE:
<223> OTHER INFORMATION: Synthetic Polynucleotide

<400> SEQUENCE: 15
acaaaaacta acacagcatg aacttggtca ccttctgagg gtgaacttgc gcacacacgt        60
cattggaaat aacatggagg tccacacact gaagtttctt tggggtcaag aactcttgtt       120
ctaaatgact agcagatact ttaggaaccc tcaaccaaaa gctaacggta aaattattaa       180
acatatcagc gctgcagact gccgcaaggg cgagcaagcc taaaatcatg tacctcatgg       240
tggtac                                                                  246

<210> SEQ ID NO 16
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 16
tctagaagcc ccaagcttac cacctgca                                           28

<210> SEQ ID NO 17
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 17
tctagatcag gggttggcca cgatggtgtc cttgatccac t                            41
```